(12) United States Patent
Houghten et al.

(10) Patent No.: US 7,166,296 B2
(45) Date of Patent: Jan. 23, 2007

(54) PHARMACEUTICAL FORMULATIONS AND LIGANDS FOR USE THEREIN; MIMETICS FOR UEA-1

(75) Inventors: Richard Houghten, Solana Beach, CA (US); Clemencia Pinilla, Cardiff, CA (US); Imelda Lambkin, Sutton (IE); Daniel O'Mahony, Blackrock (IE); Christa Hamashin, San Diego, CA (US); Amy Schink, San Diego, CA (US); Lisa Osthues-Spindler, Julian, CA (US)

(73) Assignee: Sarlan, Ltd., Hamilton (BM)

( * ) Notice: Subject to any disclaimer, the term of this patent is extended or adjusted under 35 U.S.C. 154(b) by 378 days.

(21) Appl. No.: 10/187,550

(22) Filed: Jul. 2, 2002

(65) Prior Publication Data

US 2004/0062796 A1    Apr. 1, 2004

Related U.S. Application Data

(60) Provisional application No. 60/302,868, filed on Jul. 3, 2001, provisional application No. 60/302,822, filed on Jul. 2, 2001.

(51) Int. Cl.
*A61K 9/127*     (2006.01)
*A61K 9/16*      (2006.01)
*A61K 9/50*      (2006.01)

(52) U.S. Cl. ..................... 424/450; 424/491
(58) Field of Classification Search ................ 424/450, 424/491

See application file for complete search history.

*Primary Examiner*—Bruce R. Campell
*Assistant Examiner*—B. Dell Chism
(74) *Attorney, Agent, or Firm*—Synnestvedt & Lechner LLP

(57) ABSTRACT

UEA-1 Mimetics, pharmaceutical formulations comprising them, and their uses as targeting agents for therapeutic and diagnostic purposes.

9 Claims, 7 Drawing Sheets

Reaction Scheme for Synthesis of compound carrying 'Four copies of Gallic Acid'.

Figure 2  Surface binding and uptake of MSI35-2 gallic acid
mimetic coated particles
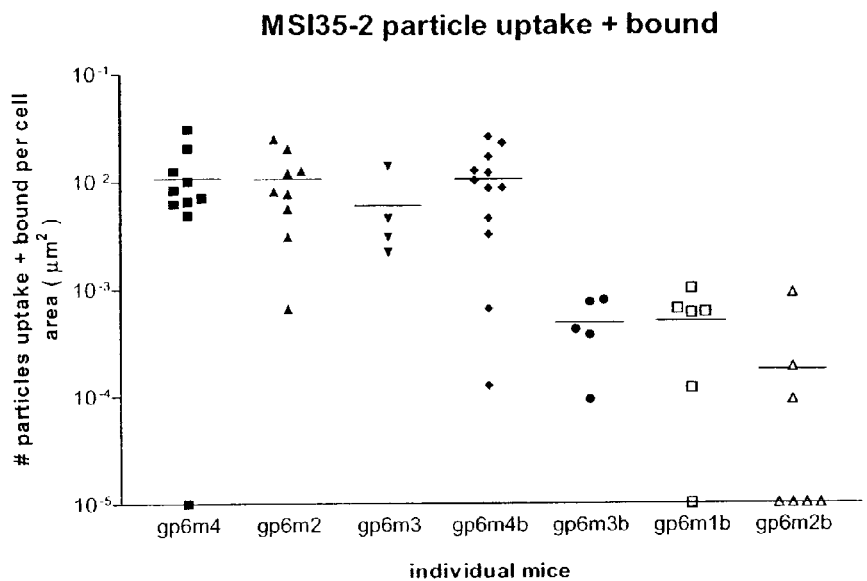
Figure 3  Surface binding and uptake of b-UEA1 coated
particles
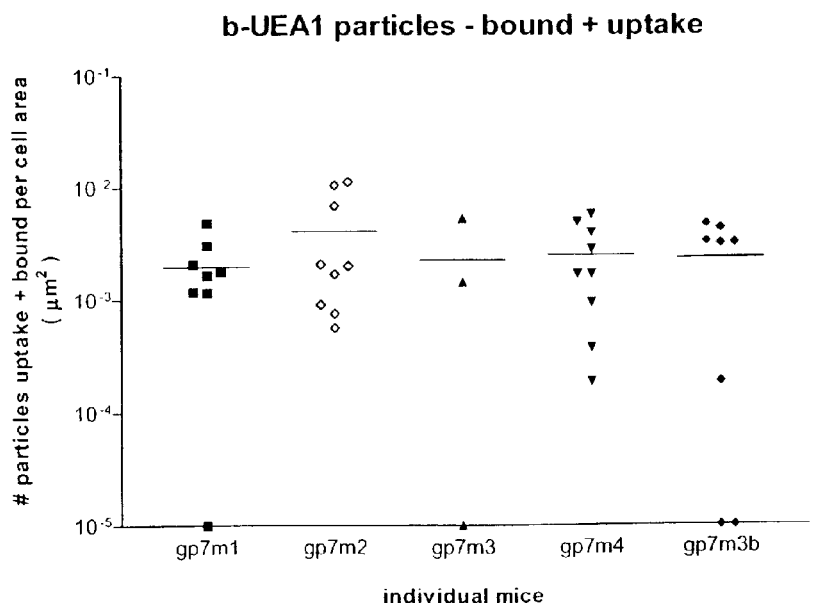

Figure 4  Surface binding & uptake of biocytin coated particles

**streptavidin control particle
uptake + bound**

Figure 5
MSI 35: Biotinylated 2-copy and 4-copy structures
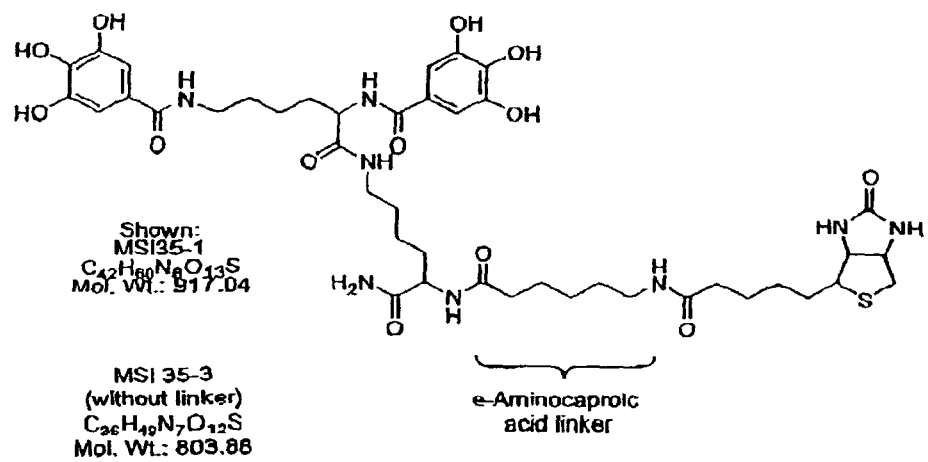
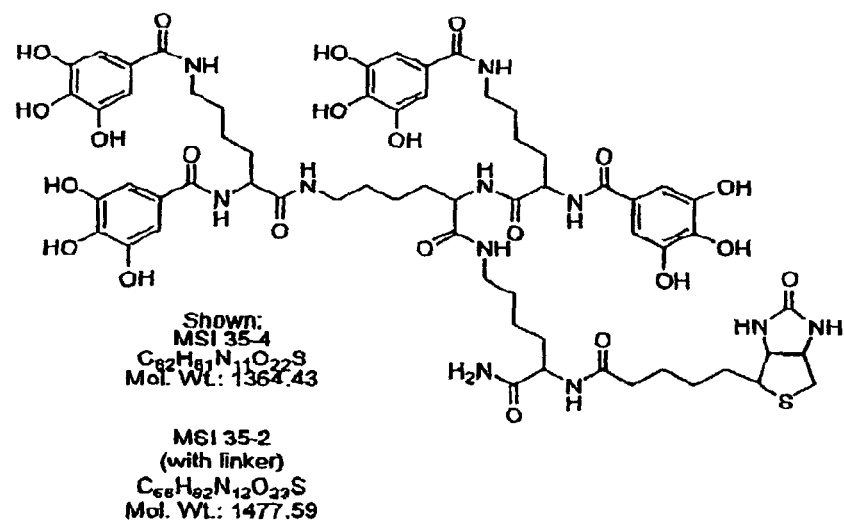

Figure 7 HUMAN GIT STUDIES - UEA1R EXPRESSION
Crohn's Disease
Crypt cells
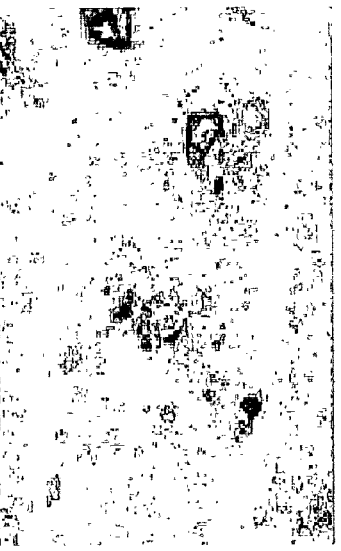
Ulcerative Colitis
Crypt cells
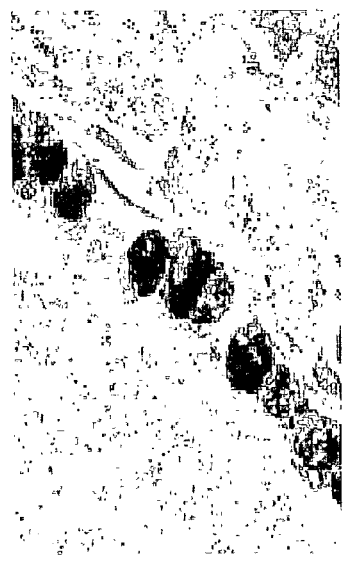
Crohn's Disease
M cells
Colon Carcinoma
Carcinoma cells

Figure 8
SynB1
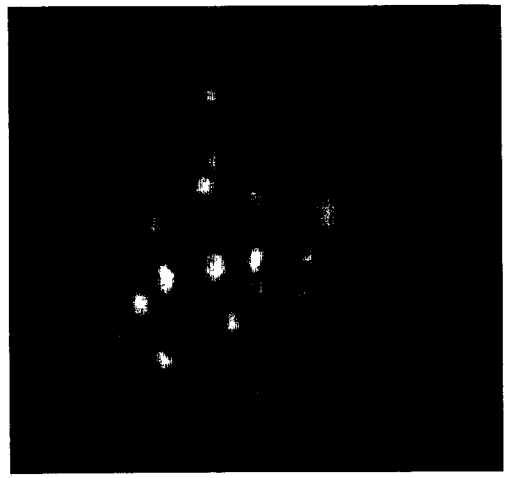
UEA-1 mimetic
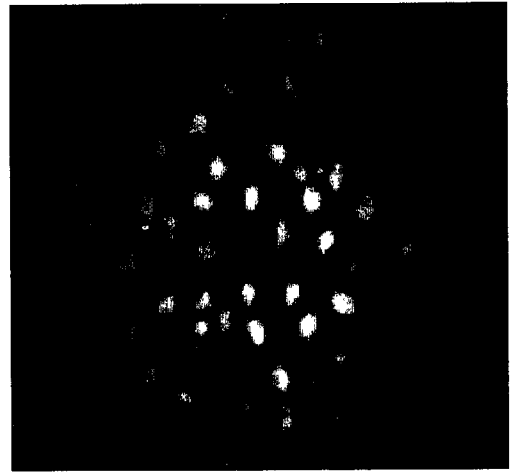
Control: no ligand
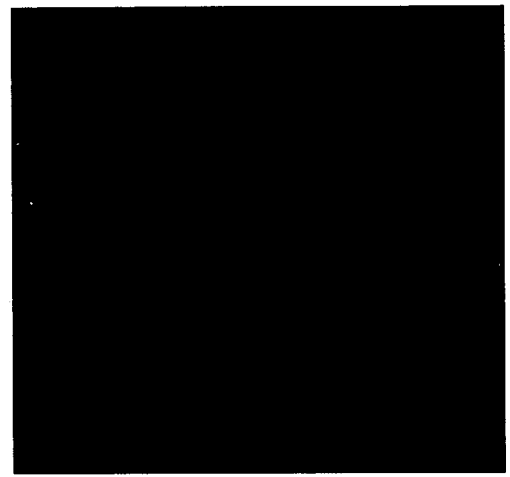
Control: negative peptide
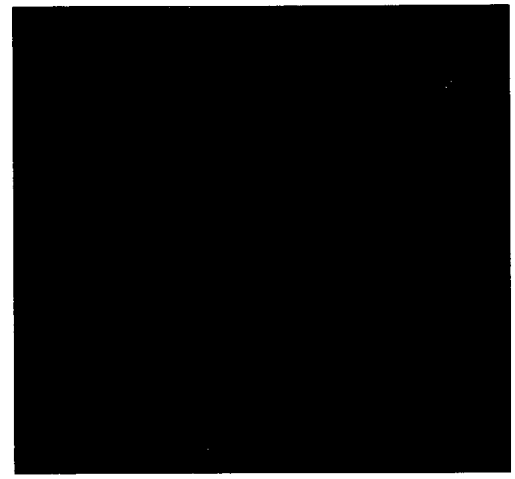

PHARMACEUTICAL FORMULATIONS AND LIGANDS FOR USE THEREIN; MIMETICS FOR UEA-1

CROSS REFERENCE TO RELATED APPLICATIONS

This application claims the benefit of U.S. provisional application Ser. No. 60/302,822, filed Jul. 2, 2001 and U.S. provisional application Ser. No. 60/302,868, filed Jul. 3, 2001, both of which are incorporated herein by reference in their entirety.

FIELD OF THE INVENTION

This invention has to do with pharmaceutical formulations, and particularly pharmaceutical formulations suitable for enteral administration, notably oral dosage forms. The invention has particular reference to adapting a pharmaceutical formulation with a view to improving the take-up of pharmaceutically-active ingredient such as a drug or vaccine through the body's epithelial layer, especially the enterocytes lining the lumenal side of the gastrointestinal tract (GIT). An aspect of the invention relates to the identification, preparation and use of categories of compounds, including novel compounds, able to be incorporated in a pharmaceutical formulation to enhance the transport of pharmaceutically-active ingredients through the epithelial layer. Such compounds include novel compounds useful for other purposes as mimetics of certain naturally-occuring compounds.

This invention also has to do with compositions and methods useful in the diagnosis and prognosis of disease states, in particular involving the imaging e.g. by staining, or marking, of certain tissue cell types from the human or animal body in order to help establish the status or condition of the tissue. In particular in one aspect the compositions disclosed herein are applied to the investigation or evaluation of cells of the gastrointestinal tract (GIT). This may be for assessment of a suspected or known condition of inflammation, neoplasia, dysplasia or other abnormal and perhaps malignant cell transformation in the cells concerned. Diseases of particular interest include colon carcinoma, ulcerative colitis and Crohn's Disease.

In another aspect the composition and methods disclosed herein are applicable to the evaluation of the disposition of blood vessels in human or animal tissue, wherever malignant or non-malignant.

BACKGROUND TO THE DRUG/VACCINE DELIVERY ASPECTS OF THE INVENTION

It is well known that the effect of a pharmaceutically-active ingredient administered to the body depends greatly on the administration route. Ideally of course one wants to create a concentration of the active ingredient localised at the affected site, but there is seldom a practical way of achieving this directly. For many drugs parenteral administration (e.g. intravenous, subcutaneous, intramuscular) is most effective but it has well known limitations and disadvantages. These include the risk of adverse effects from local high concentrations of drug substance in the body, the risk of infection at injection sites and in general a measure of discomfort or inconvenience tending to reduce patient compliance. Patient compliance is very important where a drug is to be routinely self-administered.

Other routes exploit drug transport across epithelial barriers, e.g buccal, nasal, vaginal, rectal and intestinal. Among these, enteral and particularly oral administration is by far the most convenient and favoured by patients. However enteral drug delivery is notoriously problematic because of the very indirect route by which the active ingredient enters the system. To show a therapeutic effect an orally-administered drug must survive the acidic environment of the stomach and then cross the epithelial barrier i.e. the gut lining in order to enter the circulation or interact with the immune system.

A number of published and practical proposals exist for coating and/or encapsulating pharmaceutically-active ingredients in excipients which allow the active substance to pass through the stomach and survive until they reach the target region of the GIT. One formulation type of particular current interest is the so called microparticles and nanoparticles, made of bioerodible or biodegradable polymeric excipients which can retain and protect the active substance as it travels along the GIT and then be absorbable through the gut wall, after which the particles should break down in the bloodstream and release the active ingredient to exert its therapeutic effect.

In practice however it has been found that bioavailability with these formulations is nevertheless much lower than with parenteral routes and also highly variable from one patient to another. This is generally regarded as being because of the difficulty in getting the active substance, in its bioerodible/biodegradable encapsulation where present, across the gut wall with its mucosal layer and highly selective epithelial cells.

Particular challenges in this respect arise in relation to the pharmaceutical use of biological or biotechnology products such as hormones and enzymes. These are generally macromolecular, e.g. proteins, peptides, genes, pieces of DNA, DNA vaccines, antisense oligonucleotides etc. Their large molecular size makes it difficult for them to cross the epithelium. Their stability in the GIT is poor because of the action of acids and enzymes. The bioavailability via the oral route is therefore a very low percentage, which is doubly problematic having in mind such drugs' scarcity and expense. Currently only parenteral administration is usable, with its attendant disadvantages. It would be highly desirable to improve the bioavailability of these macromolecular drugs and vaccines via other routes.

Various proposals have been published relating to means for giving drug-active particles a positive affinity to the gut wall so that whatever transepithelial mechanism operated would have a persistent presence of the active substance to work on, and/or some biochemical incentive to promote cellular uptake of the active.

Some work has been done on this and it has been pointed out and shown that various lectins—naturally-occurring protein substances with specific affinities for certain sugar residues—will bind specifically to model enterocyte-type cell lines. This is because the enterocyte surface displays oligosaccharide moieties. It has therefore been proposed to use lectins as carriers for oral drug delivery, particularly taking into account that non-toxic plant lectins are already in the human diet. Reference is made to the following publications. F. Gabor et al, Journal of Controllable Release 55 (1998), pp 131–142: N. Foster et al, Vaccine 16, No. 5 (1998), pp 536–541: C. M. Lehr et al, Pharm Res. 12 (1992) pp 547–553, and other articles on related themes.

Despite these interesting results, the use of lectins to promote "bioadhesion" of drug substances in the GIT remains problematic, because such large protein molecules are liable to degradation and loss of activity both in the gut under the action of enzymes and during processing to prepare formulations. This large size, together with potential immunogenicity and cytotoxicity effects, limits the use of lectins per se as targeting agents to deliver drugs and vaccines to and across the human GIT.

The present inventors have carried out very extensive investigations with a view to identifying, testing and preparing alternative substances showing an affinity for epithelial cells, and hence a "bioadhesive" capacity making them useful as moieties, ingredients or coatings in enterally-administered pharmaceutical formulations.

BACKGROUND TO THE DIAGNOSTIC AND PROGNOSTIC ASPECTS OF THE INVENTION

It has been noted that alteration and/or upregulation of surface sugar residues in the intestinal mucosa have been associated with malignant transformation, dysplastic changes and extensive colitis. For example, tissues from ulcerative colitis and Crohn's disease patients exhibited altered distribution of Ulex europaeus I (UEA1) labelling sites (Yoshioka et al, 1989). The expression of lectin-binding sites on human intestinal goblet mucin was specifically altered in these conditions, thus possibly providing an alternative approach to the assessment of neoplastic risk in these diseases (Yoshioka et al, 1989). Patterns of UEA1 and Dolichos biflorus agglutinin (DBA) in carcinomas of the large intestine were also altered when compared to normal mucosa and adenomas (Iwakawa et al, 1996)

UEA1 is a lectin protein of approximately 60 kDa derived from furze (Ulex europaeus) that is known to bind to fucose residues and in particular is known to bind to epithelial cells.

We have done a large amount of work investigating the properties of UEA1 and in identifying and synthesising other molecules which mimic UEA1, in the sense that they share to a lesser or greater degree (a greater degree, in some cases) the characteristic binding activity of UEA1 to epithelial cells, but because of their simpler molecular structure may enjoy any of higher stability, reduced cost, easier labelling or the possibility of use in multivalent forms. These other molecules, referred to in what follows as "UEA1 mimetics" may have any of a variety of organomolecular structures. They may be peptides, peptidomimetics and/or small organic molecules. A variety (non-limiting) of such molecules and methods of identifying and preparing them are discussed later below.

We have confirmed the effectiveness of UEA1 and of its mimics in binding to human intestinal tissue sections. In view of the relationships noted above between various disease states, we put forward the first aspect of the present invention which is methods and compositions for assessing the status of GIT cells by means of imaging, using UEA1 or a UEA1 mimetic as a localisation agent which binds characteristically to epithelial cells.

A second aspect of the invention relates to the fact that UEA1 binds specifically to the vascular endothelium of various human tissues irrespective of the blood group type or secretive status of the tissue. UEA1 staining of blood vessels has been evaluated in various studies of malignant and nonmalignant tissues. For example, most vessels in malignant and nonmalignant tissues of bladder, prostate and testis were readily identified (Fujime et al, 1984). UEA1 visualized the endothelia of blood vessels with equal intensity, sensitivity, and reliability in normal brain and in tumour tissue with neovascularization (Weber et al, 1985). While large, medium, and small vessels were equally well demonstrated by UEAL and antibodies against FVIII/RAG, capillaries and endothelial sprouts were stained more consistently and intensely by UEA1. UEA1 was also a specific and sensitive marker for the endothelial cells in benign vascular lesions (Miettinen et al, 1983). UEA1 also stained many neoplastic cells of endothelial sarcomas. Melanomas, anaplastic carcinomas, and other types of sarcomas were negative.

Since UEA1 stains blood vessels of both normal and tumour tissues with equal intensity it is not an obvious tumour vasculature-specific targeting agent. However we observe that UEA1 staining has potential application in studying distribution of vessels in relation to various normal and pathological events. Since blood vessel invasion is one of the most important diagnostic and prognostic parameters used by pathologists in the evaluation of neoplastic conditions, UEA1 and mimetics thereof such as peptides, peptidomimetics and/or small organic molecules which mimic UEA1 have value in establishing the diagnosis of lymphovascular involvement.

Thus, the use of UEA1 and its mimetics as disclosed herein in the diagnosis/prognosis of conditions by observation of vascular involvement and corresponding compositions which may be adapted for imaging as in the first aspect of the above is a further aspect of the invention.

SUMMARY OF THE INVENTION

In one general aspect, the invention is a pharmaceutical formulation comprising a pharmaceutical agent and a bioadhesive ligand, said bioadhesive ligand comprising an organocyclic (C,N, O and/or S) moiety, said organocyclic moiety a polyhydroxy- or polyalkoxy-substituted moiety (at least 2 hydroxy or 2 alkoxy groups, respectively.) Polyhydroxy-substituted organocyclic moieties are preferred. For polyalkoxy-substituted organocyclic moieties, $C_1$–$C_5$ alkoxys are preferred, and $C_1$–$C_3$ alkoxys are more preferred, where for example a $C_2$ alkoxy is ethoxy.

The ligand may be bound, either covalently or noncovalently, to a carrier entity comprising the pharmaceutical agent. The ligand is preferably bound to the surface of the carrier.

In embodiments of particular interest, the carrier entity is selected from the group consisting of a nanoparticle, a microparticle, and a liposome.

In some preferred embodiments, the backbone of the organocyclic moiety comprises a backbone, ring that consists of 5 to 7 atoms. (For purposes herein, benzene has a backbone of 6 carbon atoms in a single ring, naphthalene a backbone of 10 carbon atoms and has two backbone rings, each consisting of 6 carbon atoms, the two rings sharing two carbon atoms). The backbone ring of 5 to 7 atoms may be unsaturated (i.e., aromatic). In some highly preferred embodiments, all the atoms of the ring backbone are carbon atoms.

Preferred backbones for the organocyclic moiety are those identical to that of a radical selected from the group consisting of phenyl, napthyl, cyclohexyl, benzyl, benzoyl, pyridine and dihydrobenzopyran. It is particularly preferred that such a backbone is substituted with 2 or more hydroxy radicals, most preferably 2 to 4 hydroxy radicals. Highly preferred organocylcic moieties are galloyl or trimethoxyphenyl radicals.

In a highly preferred set of embodiments, the organocyclic moiety is covalently linked to a scaffold moiety. In one such embodiment, the bioadhesive ligand comprises two or more organocyclic moieties linked by a scaffold moiety.

Among the preferred constructs are those wherein the shortest ring-to-ring length along the scaffold and between the two organocyclic moieties is from 1 to 20 atoms. (To illustrate, in compound 2, described below, the shortest ring-to-ring length between the napthyl and chloro-phenyl radicals is 6, between the napthyl and biphenyl radicals it is 5.)

A preferred group of scaffold moieties comprises a moiety selected from the group consisting of amino acids, guanidines, hydantoins, thiohydantoins, thioureas, cathechins, acylamines, dicyclicamines, tricyclicamines, and saccharides. A scaffold comprising an amino acid is highly preferred, as are ones comprising a peptide of at least 1 amino acids (preferably 2 to 50, more preferably 2 to 20, most preferably 2 to 6 amino acids). It is also highly preferred that a trihydroxybenzoyl or trimethoxybenzyl moiety be linked (either directly or via a linker) to the amino acid or amino acids through the amide functionality. Lysine is a highly preferred amino acid for purposes of building the scaffold.

Preferably X comprises 2 to 10 organocylic moieties, each linked to the linear backbone either directly or by a linker moiety backbone that does not exceed 10 atoms.

Another preferred scaffold moiety is an acylamine. Preferred acylamines are those of the structure X—NH—(C=O)—Y, where X comprises a linear backbone comprising at least two atoms (preferably 2 to 20) selected from the group, C and N. More preferably X comprises 2 to 10 organocylic moieties, each linked to the linear backbone either directly or by a linker moiety backbone that does not exceed 10 atoms.

Y preferably comprises a polyhydroxy or polymethoxy organocyclic moiety. It is particularly preferred that such an organocylic moiety is linked to the (C=O) group of the acylamine either directly or by a linker moiety backbone that does not exceed 10 atoms. In a preferred set of embodiments, the Y moiety is selected from the group consisting of 3,4,5-trihydroxyphenyl, 3,4,5-trimethoxyphenyl, 4-biphenylmethyl, and 4-ethyl-4-biphenylmethyl. In one highly preferred embodiment, —(C=O)—Y is a galloyl group.

In one set of preferred embodiments, the R group (e.g., the cyclohexylmethyl moiety of cyclohexylalanine) of at least one amino acid is linked to the X moiety of the acylamine, said amino acid selected from the group consisting of D-Norleucine, L-norleucine, D-tyrosine, L-tyrosine, D-cyclohexylalanine, L-cyclohexylalanine, D-arginine, and L-arginine. An organocyclic moiety can be linked to the X moiety of the acyl amine, said organocyclic can for example be selected from the group consisting of D-napthylmethyl, L-napthylmethyl, and L-p-chloro-benzyl.

As regards examples of specific bioadhesive ligands, the bioadhesive ligand comprises a compound selected from the group consisting of those compounds specified in Tables 1–6, 7A, 7B, and 8, below. (The foregoing takes into account, for example, that the R1, R2, and R3 compounds in the individual columns in Tables 1, 2, and 3, were the compounds used to generate the somewhat smaller R1, R2, and R3 moieties in the chemical diagram (equivalent to —NH—CH2—CHR1—N(-)—CH2—CHR2—NH—CO—R3) immediately preceding those tables). As a result, the appearance of Nap-ala for napthylalanine as an R1 in Table 1 indicates that the corresponding R1 radical in the chemical diagram is napthylmethyl- and the appearance of 3,4,5-trimethoxybenzoic acid as an R3 in Table 1 indicates that the corresponding R3 radical in the chemical diagram is 3,4,5, trimethoxyphenyl. An analogous situation will be seen to exist for other Tables)

As to Table 4, it is preferred that the ligand comprises a compound that has a Single Tier Assay Avg % inhibition at 250.0 (μg/ml) of at least 30, more preferably at least 20.

As to Table 6, it is preferred that the ligand comprises a compound that has a Single Tier Assay IC50(50 ug/ml) less than 250, preferably less than 100, most preferably less than 30.

As to Table 7(a) it is preferred that the bioadhesive ligand comprises a 2-copy structure specified in Table 7(A) that has a 2nd Tier IC50 value (uM) of 350 uM or less, preferably less than 200 uM, more preferably less than 100 uM.

As to Table 7(b) it is preferred that the bioadhesive ligand comprises a compound that is a 4-copy structure specified as having a 2nd Tier IC50 value (uM) of 250 uM or less, more preferably less than 200 uM, even preferably less than 50 uM, most preferably less than 3 uM.

As to Table 8, it is preferred that the bioadhesive ligand comprises a compound that has an IC 50 (uM), in a 2nd tier assay, that is less than 150, preferably less than 15.

The tested compounds described in Tables 1, 2, 3, 4, 5, 6, 7, 7A, 7B, and 8 are themselves aspects of the invention.

In another general aspect, the invention is a method of administering a pharmaceutical formulation to an organism having an intestinal epithelium (preferably a mammal, most preferably a human), said method comprising administering a pharmaceutical formulation of Claim 1. In one set of embodiments of interest, the bioadhesive ligand is covalently or noncovalently bound (preferably on the surface) to a carrier comprising the pharmaceutical agent.

The present inventors have carried out very extensive investigations with a view to identifying, testing and preparing alternative substances showing an affinity for epithelial cells, and hence a "bioadhesive" capacity making them useful as moieties, ingredients or coatings in enterally-administered pharmaceutical formulations.

We screened a number of combinatorial libraries, including both peptide and non-peptide organic molecules, in competitive assays with the lectin UEA-1, a lectin protein of approximately 60 kDa derived from furze (Ulex europaeus) that is known to bind to fucose residues and in particular is known to bind to epithelial cells.

What we have found is that cyclic organic groups having two or more and preferably three or more hydroxy or hydroxy-bearing substituents can be binding-active moieties with respect to epithelial cells including epithelial cells of the intestinal tract. Organic compounds having such binding-active moieties, and particularly having two or more of them on an organic skeleton or "scaffold", can be used as bioadhesive ligands in pharmaceutical formulations.

The cyclic group may be carbocyclic or heterocyclic. It may be aromatic, non-aromatic, fused aromatic or fused partly-aromatic ring systems.

Polyhydroxy-substituted aromatic groups are preferred, e.g. diols, triols, tetrols etc of phenyl and related aryl ring systems e.g. naphthyl, or also alicyclics such as cyclohexenyl. The phenyl or related ring may be joined to a molecular skeleton or scaffold as a benzyl or benzoyl group, or the equivalent for the related ring systems.

Hydroxy groups on the ring may be vicinal.

In particular we have found good results with trihydroxyphenyl groups, which may be linked to a scaffold as trihydroxybenzyl or benzoyl.

The most preferred binding-active moiety that we have found is based on a 3,4,5-hydroxyphenyl group which may be joined to a scaffold e.g. via an amide or other acyl link, so that it constitutes a galloyl (3,4,5-hydroxybenzoyl) group.

Preferably the hydroxy groups take the —OH form, although thiol analogues and masked e.g. alkoxylated forms may also be useful.

As referred to above, we have found that good results are achieved when two or more, and preferably three or more, binding-active moieties as specified above are provided on an organomolecular scaffold or skeleton. A wide variety of options exist for this scaffold but of course it is preferably biologically compatible in the sense that it will not break down to harmful substances, and generally preferably contains nothing other than carbon, nitrogen, oxygen, sulphur and hydrogen. It may be linear, branched, cyclic or any combination of these.

Preferably the scaffold consists of hydrocarbon entities linked via functional groups. Suitable functional groups are preferably selected from but not limited to amino, amido, acyl, ether, ester, carboxylic acid and urea linkages.

In view of their established biological acceptability, molecular scaffolds based on or comprising amino acid units, and/or analogues or derivatives thereof, are preferred. The scaffold may be or comprise an amino acid, peptide, oligopeptide (preferably from 2 to 10 and more preferably from 1 to 6 amino acids) substituted with one or more and preferably plural of the binding-active moieties mentioned above. Natural or synthetic amino acids may be used in the scaffold.

Non-peptide scaffolds are also possible. The skilled person is already aware of peptidomimetic molecules and molecular frameworks of established effectiveness, and these include, among various types of molecules using the functional groups and linkages mentioned above, molecules comprising heterocyclic rings, guanidines, hydantoins, thiohydantoins, thioureas, catechins, acylamines, saccharides and so forth.

Where the scaffold comprises an amino acid, peptide, oligopeptide or analogue thereof at least one binding-active moiety may be linked at the C-terminal of the scaffold.

The scaffold may provide a linear or cyclic backbone from which the binding-active groups are branched, optionally via branch spacer chains such as hydrocarbon chains.

Links between the binding-active moieties and the scaffold may be via amino, amido, acyl, ether, alkylene, alkenylene or other suitable functionalities, or any combination of these.

While many of the binding-active compounds (ligands) proposed herein are believed to be novel, it is also possible to use existing compounds and analogues thereof such as tannic acid and the other tannins, which in general feature plural galloyl substituents on a sugar substrate. For these known substances, this is a newly-proposed use and formulation.

Considering the ligand compound as a whole (one or more binding-active moieties plus any scaffold) or multimers thereof its molecule is designed in line with conventional biochemical practice so as to be sufficiently stable in the enteric tract. By comparison with the lectins as previously discussed, the molecular weight of the ligand may be low and this, together with a suitable chemical make up, can provide stability, reduction in the potential for immunogenicity and cytotoxicity, as well as facilitating the manufacture and processing of synthetic ligands. A preferred molecular weight is less than 5000, preferably less than 2000 or 1500, but does not exclude multimers thereof.

However it should be noted that the present proposals also comprehend the possibility of providing the binding-active moieties whose effectiveness has been disclosed here on other types of molecule. For example they may be provided as substituents or grafts on a polymeric excipient used in the pharmaceutical formulation, such as a biodegradable polymer. The ligand molecule as a whole may be covalently or non-covalently bound on or into the pharmaceutical formulation. Similarly, the ligand molecule as a whole may be covalently or non-covalently bounds to a drug or antigen or adjuvant.

The novel pharmaceutical formulations exploiting these binding-active moieties and ligand compounds are one aspect of the invention. The use of the binding-active moieties and ligand compounds to enhance drug delivery in an enteric e.g. oral formulation is another aspect.

The ligand compounds proposed herein are for the most part novel, and in themselves, as UEA1 mimics, are an aspect of the invention claimed here.

The corresponding methods are also aspects of the invention claimed here, namely methods comprising the synthesis of the novel binding compounds, and methods of preparing pharmaceutical formulations comprising incorporating the ligand compounds—whether novel or not—into the formulation by blending, binding, coating or by other means.

In particular embodiments of the invention, one of the aforementioned bioadhesive ligands is covalently or non-covalently bound to a carrier entity comprising a pharmaceutical agent. For example, the carrier entity is selected from the group consisting of a nanoparticle, microparticle and liposome. It is preferred that the carrier entity have a largest dimension that is in the range of 10 nm to 500 μm, as discussed in more detail elsewhere herein. In particular embodiments of the invention, the pharmaceutical agent is a drug or therapeutic agent. In other specific embodiments, the pharmaceutical agent is a pathogen antigen.

Certain aspects of the invention involve the use of the bioadhesive ligands to target delivery of pharmaceutical agents.

In one aspect, the invention is a method of administering a pharmaceutical agent to an organism having intestinal epithelium, said method comprising contacting said intestinal epithelium with one of the aforementioned bioadhesive ligands that is covalently, or non-covalently bound to, a carrier entity. In preferred the embodiments, the organism is a mammal. Most preferably, the mammal is a human.

In particular embodiments of the method, the carrier entity is from the group consisting of a nanoparticle, microparticle or liposome. Preferably, the carrier entity has its major dimension in the range of 10 nm to 500 μm. In preferred embodiments, the carrier entity drug-loaded or drug-encapsulated. The preferred route of administration for delivery of the ligand-carrier entity is the oral route. Other possible routes are the rectal, subcutaneous, intramuscular and intravenous routes.

As used herein, the term "carrier entity" is defined as a particle or droplet that can carry a pharmaceutical agent. A microparticle is defined as a particle whose major dimension in the range 1 to 5 μm, most preferably in the range 1 to 3 μm. A nanoparticle is defined as a particle whose major dimension is less than 1μ, preferably in the range 1nm to 500 nm, most preferably in the range 10 nm to 500 nm.

As used herein, the major dimension of a spherical particle is its diameter, or a rod shaped particle, its length. For other particles, it is the longest dimension possible for the particle.

Nano- and microparticles that are loaded with, or encapsulate, pharmaceutical agents, can be coated with the bioadhesive ligands, such as those of the present invention, that target intestinal epithelium tissue. The coating can be effected by covalent or non-covalent bonding. The covalent bonding can be achieved by adsorption or any other coating process. In either case, the bonding can be made to completed particles or to particle components that subsequently form part of the particles.

Biodegradable particles are preferred.

Pharmaceutical agents can, in the alternative, be directly linked a bioadhesive ligand.

A "pharmaceutical agent" is a therapeutic or diagnostic agent. Therapeutic agents are those that are administered either to treat an existing disease or prophylactically to protect against a potential future disease. Diagnostic agents are any agents that are administered as part of a diagnostic procedure.

Examples of therapeutic agents are drugs, genes, gene-delivery vectors, and antigens/vaccines.

Drugs include, for example, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents, antisense oligonucleotides, gene-correcting hybrid oligonucleotides, ribozymes, RNA interference (RNAi) oligonucleotides, silencing RNA (siRNA) oligonucleotides, aptameric oligonucleotides and triple-helix forming oligonucleotides, DNA vaccines, adjuvants, recombinant viruses.

Examples of gene-delivery vectors are DNA molecules, viral vectors (E.g. adenovirus, adeono-associated virus, retroviruses, herpes simplex virus, and sindbus virus), and cationic lipid-coated DNA and DNA-dendrimers.

Drugs include conventional small molecule drugs, proteins, oligopeptides, peptides, and glycoproteins.

Examples of drugs are as insulin, calcitonin, calcitonin gene regulating protein, atrial natriuretic protein, colony stimulating factor, betaseron, erythropoietin (EPO), interferons (E.g. α, β or γ interferon), somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII and interleukins (E.g. interleukin-2). Representative drugs also include: analgesics (E.g. fentanyl, sufentanil, butorphanol, buprenorphine, levorphanol, morphine, hydromorphone, hydrocodone, oxymorphone, methadone, lidocaine, bupivacaine, diclofenac, naproxen and paverin); anti-migraine agents (E.g. sumatriptan and ergot alkaloids); anti-coagulant agents (E.g. heparin and hirudin); anti-emetic agents (E.g. scopolamine, ondansetron, domperidone and metoclopramide); cardiovascular agents, anti-hypertensive agents and vasodilators (E.g. diltizem, clonidine, nifedipine, verapamil, isosorbide-5-mononitrate, organic nitrates and agents used in treatment of heart disorders); sedatives (E.g. benzodiazepines and phenothiozines); narcotic antagonists (E.g. naltrexone and naloxone); chelating agents (E.g. deferoxamine); anti-diuretic agents (E.g. desmopressin and vasopressin); anti-anginal agents (E.g. nitroglycerine); anti-neoplastics (E.g. 5-fluorouracil and bleomycin); prostaglandins; and chemotherapy agents (E.g. vincristine).

Examples of antigens that are therapeutic agents are tumor antigens, pathogen antigens and allergen antigens. A vaccine preparation will contain at least one antigen. "Pathogen antigens" are those characteristic of pathogens, such as antigens derived from viruses, bacteria, parasites or fungi.

Examples of important pathogens include vibrio choleras, enterotoxigenic *E. Coli*, rotavirus, *Clostridium difficile*, Shigella species, *Salmonella typhi*, parainfluenza virus, influenza virus, *Streptococcus mutans*, *Plasmodium falciparum*, *Staphylococcus aureus*, rabies virus and Epstein-Barr virus.

Viruses in general include the following families: *picronaviridae; caliciviridae, togaviridae; flaviviridae; coronaviridae; rhabodviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae and poxyviridae.*

Bacteria in general include but are not limited to: *P. aeruginosa; E. coli; Klebsiella* sp.; *Serratia* sp; *Pseudomanas* sp.; *P. cepacia; Acinetobacter* sp.; *S. epidermis; E. faecalis; S. pneumonias; S. aureus; Haemophilus* sp.; *Neisseria* sp.; *N. meningitidis; Bacterodies* sp.; *Citrobacter* sp.; *Branhamella* sp.; *Salmonelia* sp.; *Shigella* sp.; *S. Lesteria* sp., *Pasteurella multocida; Streptobacillus* sp.; *S. pyogenes; Proteus* sp.; *Clostridium* sp.; *Erysipelothrix* sp.; *Spirillum* sp.; *Fusospirocheta* sp.; *Treponema pallidum; Borrelia* sp.; *Actinomycetes; Mycoplasma* sp.; *Chlamydia* sp.; *Rickettsia* sp., *Spirchaeta; Legionella* sp.; *Mycobacteria* sp.; *Urealplasma* sp.; *Streptomyces* sp.; *Trichomoras* sp.; and *P. mirabilis*

Parasites include but are not limited to: *Plasmodium falciparum, P. vivax, P. ovale, P. malaria; Toxoplasma gondii; Leishmania mexicana, L. tropica, L.major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobus vermiculoarus; Taenia solium, T. saginata, Trichomonas vaginitis, T. hominis, T. tenax; Giardia lamblia; Cryptosporidium parvum; Pneumocytis carinii, Babesia bovis, B. divergens, B. microti, Isospore belli, L. hominis; Dientamoeba fragiles; Onchocerca volvulus; Ascaris luinbricoides; Necator americanis; Ancylostoma duodenale; Strongyloides stercoralis; Capillaria philippinensis; Angiostrongylys cantonensis; Hymenolepis nan; Diphyllobothrium latum; Echinococcus granulosus, E.multilocularis; Paragonimus westermani, P. caliensis; Chlonorchis sinensis; Opisthorchis felineas, G. Viverini, Fasciola hepatica, Sarcoptes scabiei, Pediculus humanus; Phtirius pubis*; and *Dermatobia hominis*.

Fungi in general include but are not limited to: *Crytpococcus neoformans; Blastomyces dematitidis; Aiellomyces dermatitidis Histoplasfrai capsulatum; Coccidiodes immitis; Candids* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunnighammella* species; *Apophysomyces* species, including *A. saksenaea, A. mucor* and *A. absidia; Sporothrix schenckii, Paracoccidioides brasiliensis; Pseudallescheria boydii, Torulopsis glabrata*; and *Dermatophyres* species.

Antigens that are allergens can be haptens, or antigens derived from pollens, dust, molds, spores, dander, insects and foods. Specific examples include the urusiols of *Toxicodendron* species and the sesquiterpenoid lactones.

Examples of adjuvants: Freund's Complete Adjuvant, Freund's Incomplete Adjuvant, Hunter's Titermax, Gerbu Adjuvant, Ribi's Adjuvant, Montanide ISA Adjuvant, Aluminum Salt Adjuvants and Nitrocellulose adsorbed protein.

In another general aspect we have confirmed the effectiveness of UEA1 and of its mimics in binding to human intestinal tissue sections. In view of the relationships noted above between various disease states, we put forward the first aspect of the present invention which is methods and compositions for assessing the status of GIT cells by means of imaging, using UEA1 or a UEA1 mimetic as a localisation agent which binds characteristically to epithelial cells.

Relevant disease states include any of those mentioned above, for example, colon carcinoma, ulcerative colitis and Crohn's Disease. The UEA1 or UEA1 mimetic localisation agent may be exploited for diagnostic/prognostic imaging in any of a variety of ways and these may in themselves be conventional. For example the UEA1 and the UEA1 mimetic may be used in an immunoassay procedure with an antibody therefor or other specific binding substance, and an imaging agent or agents (e.g. a colour staining test kit) for providing a characteristic image/colour when reacted with the antibody or other specific binding substance.

Alternatively UEA1 or UEA1 mimetic may be directly labelled, e.g. biotinylated or by some other means, so that its bound presence on the test cells can be verified by reaction with avidin or the appropriate other imaging substance(s) or test for the type of label used. Other possibilities include NMR imaging and radiolabelling.

Compositions for the present purpose may comprise the UEA1 or UEA1 mimetics, which may be labelled, as part of a diagnostic/prognostic imaging kit including any necessary complementary binding substances and imaging media.

The use of UEA1 and its mimetics as disclosed herein in the diagnosis/prognosis of conditions by observation of vascular involvement and corresponding compositions which may be adapted for imaging as in the first aspect of the above is a further aspect of the invention.

BRIEF DESCRIPTION OF DRAWINGS

FIG. 2 Surface binding and uptake of MSI35-2 gallic acid mimetic coated particles.
FIG. 3 Surface binding and uptake of UEA1 coated particles.
FIG. 4 Surface binding & uptake of biocytin mimetic coated particles.
FIG. 5 MSI 35: Biotinylated 2-copy and 4-copy structures.
FIGS. 6 and 7. Stained human tissue samples.
FIG. 8 Endothelial cell permeability assay.

DETAILED DESCRIPTION

Figure 1:
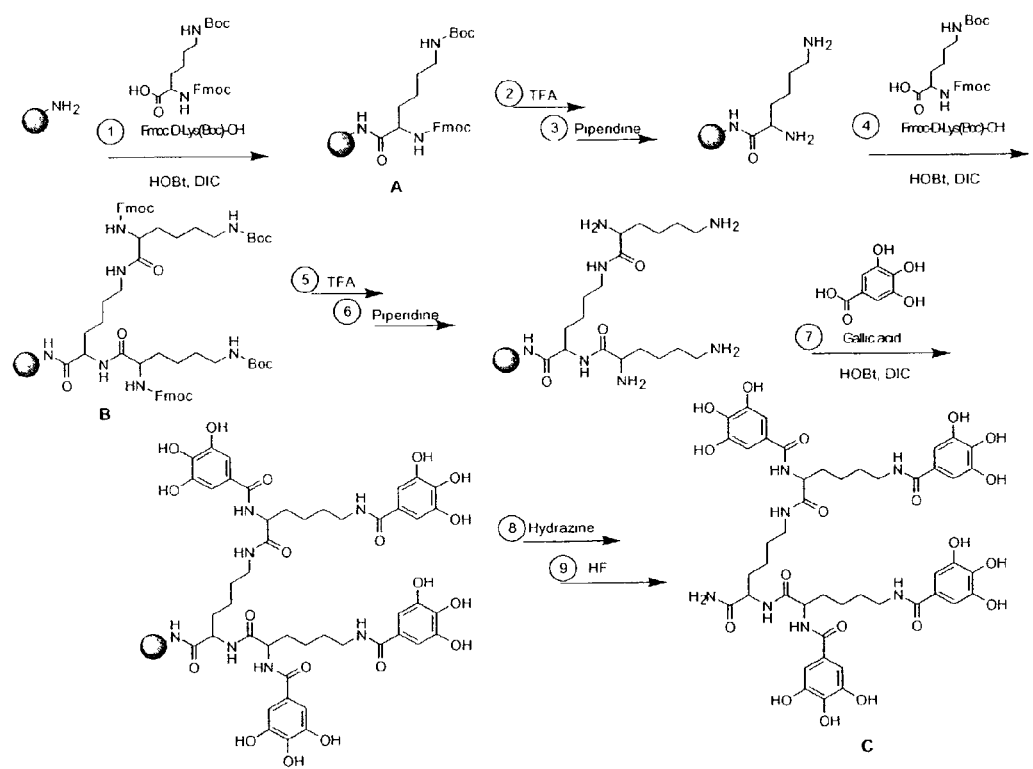
FIG. 1 Synthesis of compounds having four copies of gallic acid.

There now follows a detailed description of those aspects of our experimental work leading to the identification of the particular binding-active moieties disclosed herein, ligand compounds bearing them, verification of their activity and various examples of ligand compounds embodying the invention.

The search for small molecular weight ligands capable of binding surface receptors of epithelial cells began with the screening of various combinatorial libraries, which contained both peptides and non-peptide (organic) molecules. These libraries were synthesized in positional scanning format in which oligopeptide mixture sets comprise one predetermined residue at a single predetermined position of the oligopeptide chain (Pinilla et al. U.S. Pat. No. 5,556,762, Pinilla et al. 1992. BioTechniques. Vol 13, No 6).

The epithelial cell binding ability of compounds and mixtures obtained from synthetic combinatorial libraries was determined by competition assays. These assays were set up to measure the inhibition of binding of biotinylated UEA-1 to membrane preparations of the epithelial cell line Caco-2 (colon carcinoma cells-2), by compounds and mixtures of the combinatorial libraries. This cell line is a conventional model for epithelial cells. The ability of a compound or compounds to inhibit UEA-1 binding would suggest that this chemical itself was binding to fucose residues on the surface of epithelial cells and was hence a potential ligand.

Two competition inhibition assays were used in this case, namely single tier and two tier assays. These assays differed from each other in that in the single tier assay, the mixtures/compounds and the biotinylated UEA-1 were incubated together with the Caco-2 cell membrane preparations, while in case of the two-tier assay, the mixture/compounds were allowed to incubate alone with the cell membranes in the absence of biotinylated UEA-1, which was added in the next step. Addition of the extra step in the two-tier assay was to ensure that the compounds inhibiting the binding of biotinylated UEA-1 to the Caco-2 cell membranes were doing so by themselves binding to surface receptors on the Caco-2 cells and not to the biotinylated UEA-1. Each assay will be described in detail.

Preparation of Caco-2 Cell Membrane (P100) and Cytosolic (S100) Fractions:

1. Confluent Caco-2 cell monolayers (grown in 75 cm$^2$ flasks for up to 1 week at 37° C. and 5% $CO_2$) were washed twice in Dulbecco's PBS (DPBS).
2. Cell monolayers were treated with 10 mM EDTA-DPBS for 5–10 min at 37° C. and cells were harvested by centrifugation at 1000 rpm for 5 min.
3. Cells were washed 3 times in DPBS.
4. The cell pellet was resuspended in 3 volumes of ice cold HED buffer (20 mM HEPES (pH 7.67), 1 mM EGTA, 0.5 mM dithiothreitol, 1 mM phenylmethylsulphonyl fluoride (PMSF)) and the cells were allowed to swell for 5 min on ice.
5. The cells were homogenised for 30 sec.
6. The homogenates were centrifuged in hard walled tubes at 40,000 rpm for 45 min at 4° C.
7. The supernatant (S100) was removed and the pellet (P100) was resuspended in HEDG buffer (20 mM HEPES (pH 7.67), 1 mM EGTA, 0.5 mM dithiothreitol, 100 mM NaCl, 10% glycerol, 1 mM PMSF): 3 volumes of buffer were added, the pellet was resuspended and centrifuged at 1000 rpm for 2 min. The supernatant was removed and stored on ice. The procedure was repeated adding the second supernatant to the first.
8. The protein concentration was determined using e.g. a Bio-Rad protein assay.
9. All fractions were stored at −80° C. prior to use.

Single Tier Assays:

1. 96-well microtiter plates were coated with membrane preparations of Caco-2 cells either by allowing them to incubate on the plates for 2½ hours at room temperature or by incubating them overnight at 4° C. 100 μl of 10 μg/ml (in 0.05 M carbonate buffer, pH 9.6) of membrane preparation was added to each well.
2. The plates were flicked out, patted dry and blocked with bovine serum albumin (BSA)/DPBS (200 μl/well) for 1 to 4 hours at room temperature after which they were washed three times in water.
3. 50 μl/well (in 1.5% BSA/DPBS) of the mixtures/compounds from the combinatorial libraries were added to the wells. Control wells were also set up in which the Caco-2 cell membrane preparations were incubated with unconjugated UEA-1. A 1 in 4 dilution series of this control compound was set up starting from 0.04 μg/ml to 160 μg/ml (50 μl/well in 1.5% BSA/DPBS).

4. Biotinylated UEA-1 at a final concentration of 1 μg/ml (50 μl in 1.5% BSA/DPBS) was added to each well and the plates were left to incubate overnight at 4° C.
5. Following overnight incubation the plates were washed thoroughly (3–6 times). The plates were flicked out, patted dry and biotinylated UEA-1 was detected with commercial Streptavidin conjugated to horseradish peroxidase (HRP) (CalBiochem). This reagent was added to each well at a 1:5000 dilution prepared in 1.5% BSA-DPBS such that 100 μl of the reagent was added to each well to achieve the final concentration. The plates were left to incubate for an hour at room temperature.
6. The plates were then washed 3–6 times and the biotin-streptavidin binding was detected by adding an HRP substrate OPD (orthophenyl diamine) to each well. 100 μl/well of this substrate at a final concentration of 1.6 mg/ml was added to each well. Before adding to the wells, this substrate was activated by addition of 50 μl of 3% $H_2O_2$ per plate and the reaction was allowed to develop in the dark.
7. The reaction was stopped by adding 50 μl of 4 N $H_2SO_4$ to each well after approximately 5–10 minutes or when sufficient colour had developed. The $OD_{490}$ (absorbance at 490 nm) of each well was measured using a conventional 96 well plate reading spectrophotometer.

Two Tier Assays:
1. 96 well plates were coated with Caco-2 cell membrane preparations in the same manner as described in the single tier assay.
2. Plates were flicked out, patted dry and blocked with 1.5% BSA-DPBS (200 μl/well) for 1–4 hours at room temperature and then washed three times in water.
3. The compounds/mixtures from various combinatorial libraries were then added to individual wells (100 μl/well in 1.5% BSA-DPBS). Control wells were also set up containing a range of concentrations of purified UEA-1 which were set up as 1 in 4 dilutions starting from 0.04 μg/ml to 160 μg/ml. 100 μl at these final concentrations were added to each well.
4. The plates were then left to incubate overnight, a step that would allow the mixtures and compounds to interact with the Caco-2 cell membranes without the presence of the competitor (biotinylated UEA-1) itself.
5. Following overnight incubation, the plates were washed thoroughly in water 3–6 times.
6. 100 μl/well of biotinylated UEA-1 at a final concentration of 1 μg/ml in 1.5% BSA-DPBS was added to each well and the plates were allowed to incubate for two hours at room temperature.
7. After washing the plates 3–6 times, biotin was detected by use of commercial Streptavidin conjugated to HRP, which was added to each well at a 1:5000 dilution prepared in 1.5% BSA/DPBS such that 100 μl of the reagent was added to each well to achieve the final concentration. The plates were left at room temperature for an hour.
8. After 3–6 washes, 100 μl/well of OPD (final concentration 1.6 mg/ml) activated by $H_2O_2$ was added to each well and the reaction was allowed to develop in the dark.
9. The reaction was stopped by adding 50 μl of 4 N $H_2SO_4$ after approximately 10–15 minutes or when sufficient colour had developed.
10. The absorbance at 490 nm of each plate was measured by spectrophotometry.

Results:
The results are illustrated as the percentage inhibitory activity or the $IC_{50}$ (the concentration of the compound at which 50% inhibition of UEA-1 was reported). The absorbance at 490 nm of the unconjugated UEA-1 controls (1:4 dilutions: 160 μg/ml to 0.04 μg/ml) was used to set up a standard curve. The highest concentration of unconjugated UEA-1 was 160 μg/ml and wells containing this level of protein showed little or no colour change, as high levels of previously incubated UEA-1 bound to the majority of UEA-1 binding sites on the Caco-2 membrane preparations, thereby leaving no sites for biotinylated UEA-1 (added later) to bind to and hence no biotinylated UEA-1 was detected.

Wells containing 0.04 μg/ml of unconjugated UEA-1 showed high absorbance at 490 nm as low concentration of UEA-1 meant that most UEA-1 receptors were left unbound, which allowed biotinylated UEA-1 to bind to these receptors on the Caco-2 cell membranes, thus resulting in high absorbance of these wells at 490 nm. The absorbance at 160 μg/ml was taken as 100% inhibition and the absorbance at the other end of the scale (0.01 μg/ml) was taken as 0% inhibition. The percentage inhibition of each compound or mixtures of compounds was estimated from similar binding curves. The $IC_{50}$ values of the active compounds was determined using serial dilutions of each compound.

Using combinatorial chemistry, a large number of diverse chemical compounds, both peptide and non-peptide (organic) referred to as libraries were tested in single and two tier assays. Each library comprises a common scaffold or framework. Compounds of each library are synthesized by arranging a wide range of side chains and groups both branched and linear in different sequences on the scaffold backbone. In a different library the same elements can be arranged in a similar manner or in a different manner on another type of scaffold (for reference see Meyer et al., U.S. Pat. No. 5,859,190, Houghten, U.S. Pat. No. 4,631,211, Pinilla, U.S. Pat. No. 5,556,762). By way of example, some of the organic backbones used in combinatorial chemistry are listed below. The libraries screened in order to identify the active compounds of the invention were not limited to the backbone structures defined below.

Guanidine

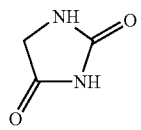

Hydantoin

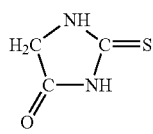

Thiohydantoin

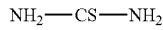

Thiourea

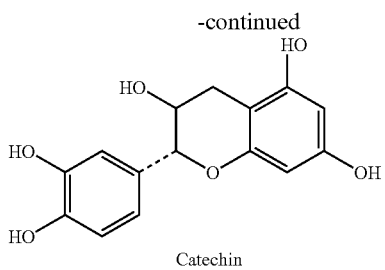

Catechin

Amongst the wide range of libraries tested, mixtures from thiohydantoin based, N-6-acylamino bicycylic guanidine based, N-acylamine based and polyphenylurea based libraries showed high inhibitory activity. To narrow the search, individual compounds from these active mixtures were deconvoluted and each tested for inhibitory activity. Results revealed that individual purified compounds from most libraries showed inhibitory activity. These included compounds from the N-acylamine-based libraries. A structure of such acylamines is e.g. as represented by formula A.

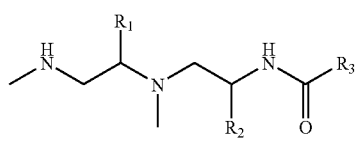
(A)

The acylamines were synthesized on solid phase resin. Here R1 and R2 groups were derived from amino acids that were coupled using conventional tBOC chemistry which involves blocking the N terminus of each incoming amino acid by BOC (N-tertbutoxyl carbonyl) to avoid its participation in the reaction. The N terminus is unblocked once the amino acid is attached. In case of synthesis of acylamines, the amide bonds of the amino acids were first methylated and then reduced to amines. The N-terminus of the developing chain was acylated with a carboxylic acid adding R3. The amine seen on the left side of the molecule was derived from the solid phase mBHA resin which has an amino group extending out that reacts with the carboxy terminus of the incoming amino acid. Cleavage of this amine from the solid support during incubation with hydrogen fluoride results in the release of this amino group thus forming the amino terminus of the acylamine.

The scheme is shown below.

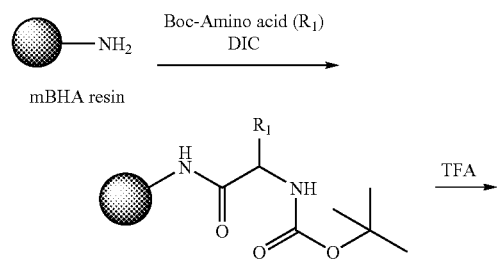

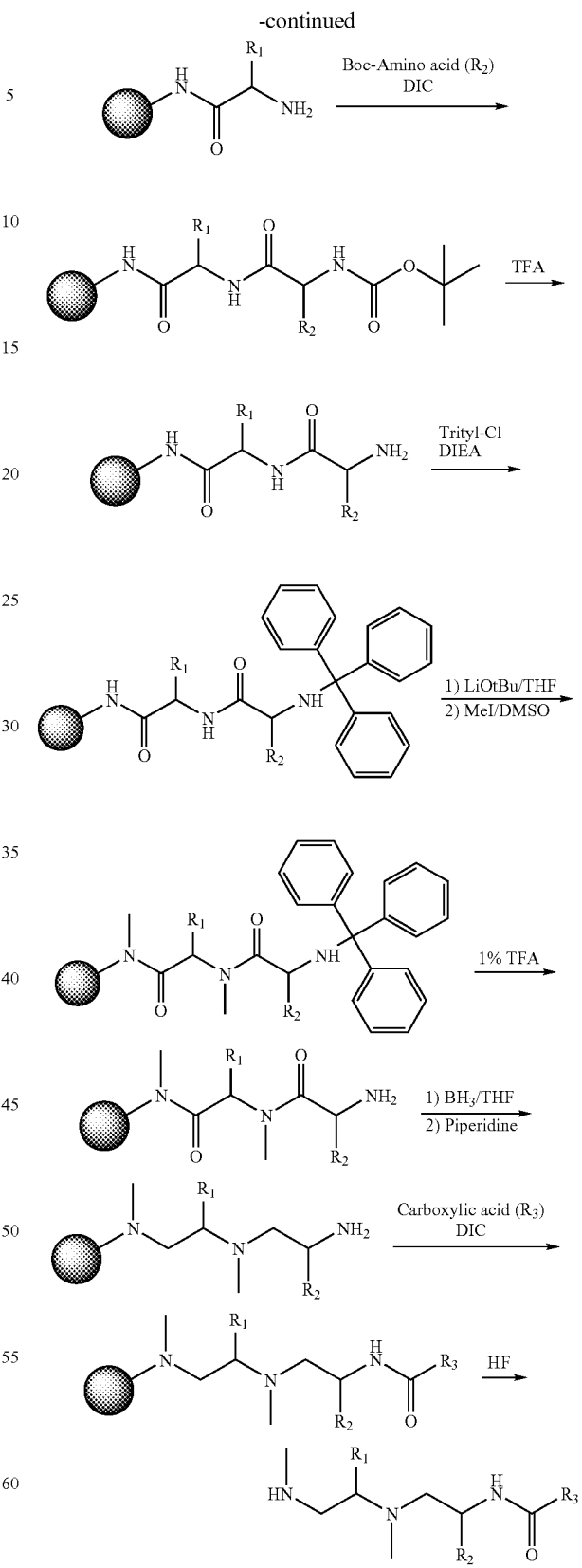

Tables 1, 2 and 3 show the inhibitory activity of compounds belonging to three N-acylamine-based libraries.

TABLE 1

| R1 | R2 | R3 | 50 µg/ml Av % Inhibition | 250 µg/ml Av % Inhibition | 50 µg/ml Av % Inhibition | 250 µg/ml Av % Inhibition |
|---|---|---|---|---|---|---|
| 5 Nap-ala | Nap-Ala | 3,4,5-Trimethoxybenzoic Acid | 16 | 54 | 39 | 51 |
| 8 Nap-ala | Nap-ala | 4-Biphenylacetic Acid | 59 | 85 | 0 | 50 |
| 10 Nap-ala | Nap-ala | 3,4,5-Trimethoxybenzoic Acid | −65 | 41 | 24 | 66 |
| 20 Nap-Ala | Nap-ala | 3,4,5-Trimethoxybenzoic Acid | −121 | 24 | 52 | 75 |
| 23 pCl-F | Nap-Ala | 4-Biphenylacetic Acid | 52 | 21 | 39 | 59 |
| 25 pCl-F | Nap-Ala | 3,4,5-Trimethoxybenzoic Acid | −173 | 66 | 65 | 63 |
| 26 pCl-F | Nap-ala | 4-Ethyl-4-Biphenylcarboxylic Acid | −116 | −2 | 39 | 56 |

Av % Inhibition:- Average Percent Inhibition

TABLE 2

| | N-acyl triamine Library TP1012 | | Two Tier Assay | |
|---|---|---|---|---|
| | | | 50 µg/ml | 250 µg/ml |
| | R1 | R2 | R3 | Avg % Inhib | Avg % Inhib |

| | R1 | R2 | R3 | Avg % Inhib | Avg % Inhib |
|---|---|---|---|---|---|
| 86 | D-Nle | D-chAla | Gallic acid | 61.61308 | 76.22587 |
| 125 | L-Leu | L-Phe | Gallic acid | 61.02335 | 77.78063 |
| 87 | D-Nle | D-Arg(Tsl) | Gallic acid | 55.81319 | 65.64472 |
| 84 | L-Tyr(Brz) | L-chAla | Gallic acid | 54.9682 | 70.64093 |
| 92 | L-Nle | D-chAla | Gallic acid | 54.8899 | 67.69989 |
| 90 | D-Nle | L-chAla | Gallic acid | 53.65788 | 69.94 |
| 91 | L-Nle | L-Tyr(Brz) | Gallic acid | 53.05769 | 65.97437 |
| 94 | L-Nle | L-Arg(Tsl) | Gallic acid | 51.51322 | 66.36993 |
| 78 | D-Tyr | L-chAla | Gallic acid | 47.10349 | 61.0039 |
| 93 | L-Nle | D-Arg(Tsl) | Gallic acid | 46.83358 | 58.5174 |
| 85 | D-Nle | L-Tyr(Brz) | Gallic acid | 46.51721 | 66.21152 |
| 96 | L-Nle | L-chAla | Gallic acid | 42.93428 | 65.78116 |
| 74 | D-Tyr | D-chAla | Gallic acid | 42.91734 | 57.91947 |
| 144 | L -pF-Phe | L -pF-Phe | a,a,a-(Trifluoro-m-Tolyl)acetic acid | 42.26244 | 66.71332 |
| 89 | D-Nle | D-Tyr | Gallic acid | 42.12294 | 65.78345 |
| 95 | L-Nle | D-Tyr | Gallic acid | 41.98644 | 66.4157 |
| 141 | L -pF-Phe | L -pF-Phe | 3,4 DichloroPhenylacetic acid | 41.43191 | 72.63565 |
| 75 | D-Tyr | D-Arg(Tsl) | Gallic acid | 40.14659 | 51.4412 |
| 88 | D-Nle | L-Arg(Tsl) | Gallic acid | 38.0323 | 59.11027 |
| 82 | L-Tyr(Brz) | L-Arg(Tsl) | Gallic acid | 37.9772 | 55.92339 |

Av % Inhibition:- Average Percent Inhibition

TABLE 3

| | | | Single Tier Assay | | Two Tier Assay | |
|---|---|---|---|---|---|---|
| | Acylamine Library MSI 22 | | 62.5 | 250 | 62.5 | 250 |
| R1 | R2 | R3 | µg/ml | µg/ml | µg/ml | µg/ml |
| L-NapAla | L-pCl-Phe | Gallic Acid | 31.5 | 46.9 | 26.7 | 54.7 |
| D-Nve | D-chAla | Gallic Acid | 22.0 | 47.8 | 20.6 | 48.5 |
| D-Tyr (Et) | D-Arg(Tos) | Gallic Acid | 27.2 | 48 | 30 | 61 |
| D-Tyr (Et) | L-chAla | Gallic Acid | 8.5 | 33.3 | 31.8 | 52.7 |
| D-Nve | D-Val | Gallic Acid | 13.7 | 46 | 12.1 | 29.8 |
| D-Tyr-(BrZ) | L-chAla | 3,4,5-Trimethoxy benzoic Acid | −0 | −11.7 | 39.7 | 58.9 |
| D-Napala | L-pCl-Phe | Gallic Acid | −14.7 | 7.4 | 23.4 | 43.7 |
| D-Napala | D-Val | Gallic Acid | 4.7 | 26.8 | 24.2 | 46.9 |
| L-NapAla | D-Napala | Gallic Acid | −3 | 7 | 22.0 | 44.6 |
| D-Tyr (Et) | L-chAla | 3,4,5-Trimethoxy benzoic Acid | −9 | −55.7 | 49.8 | 43.8 |

Av % Inhibition:- Average Percent Inhibition

Compounds in these libraries have the same N-acylamine scaffold but differ in the arrangement of side groups on each scaffold. Library TPI 1066 (Table 1) for example contains compounds with aromatic functionalities, library TPI 1012 (Table 2) contains compounds with aromatic and non aromatic functionalities are arranged on a N-acylamine based scaffold, and compounds from library MSI 22 (Table 3) are a combination of the first two libraries, in that the N-acylamine scaffold has both aromatic groups and amino acids attached to it; results are illustrated as the average percent inhibition by 50 µg/ml or 250 µg/ml of these compounds. Note that the compounds from MSI 22 were tested at doubling dilutions. Results are illustrated as the average percent inhibition by 62.5 µg/ml or 250 µg/ml of these compounds. Structures of some of the synthetic compounds tested from TPI 1066 are shown below:

Acylamine structures from TPI 1066

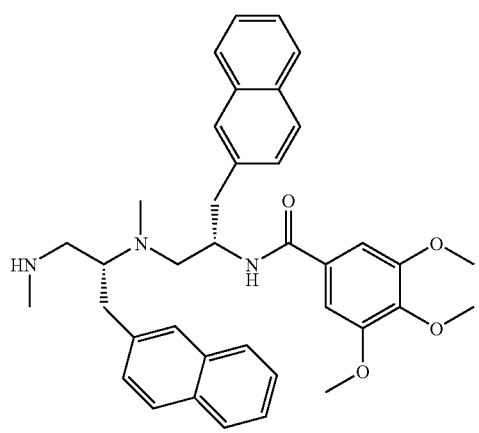

1066 #5

R1 = d-Naphthylalanine
R2 = L-Naphthylalanine
R3 = 3, 4, 5-trimethoxybenzoic acid

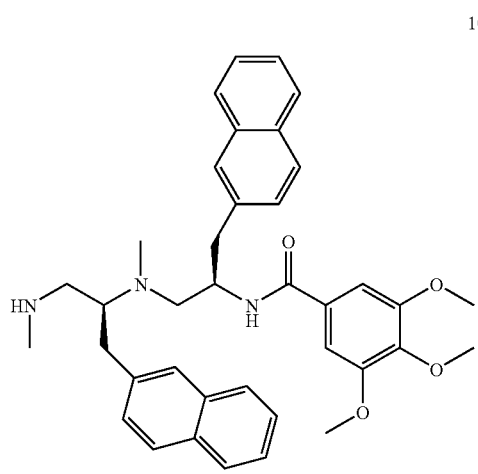

1066 #20

R1 = L-Naphthylalanine
R2 = d-Naphthylalanine
R3 = 3, 4, 5-trimethoxybenzoic acid

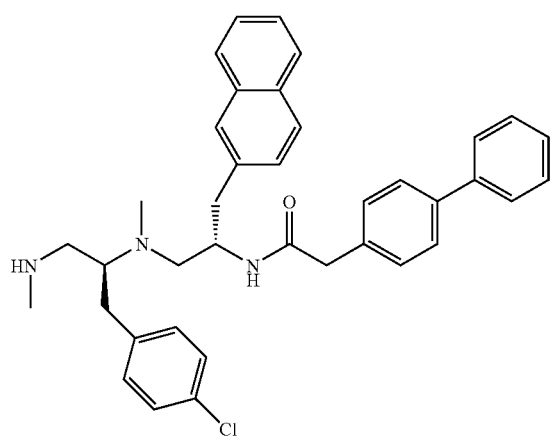

1066 #23)

R1 = L-p-chloro-Phenylalanine
R2 = L-Naphthylalanine
R3 = 4-Biphenyl acetic acid -continued

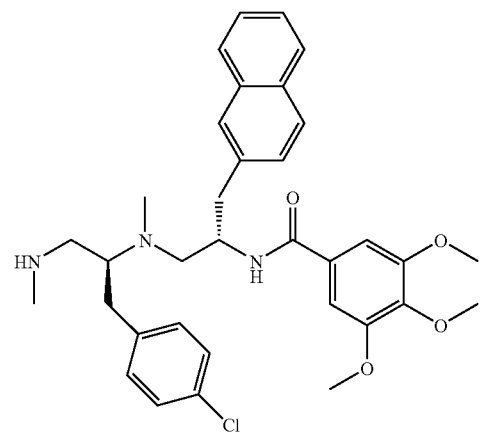

1066 #25

R1 = L-p-chloro-Phenylalanine
R2 = L-Naphthylalanine
R3 = 3, 4, 5-trimethoxybenzoic acid

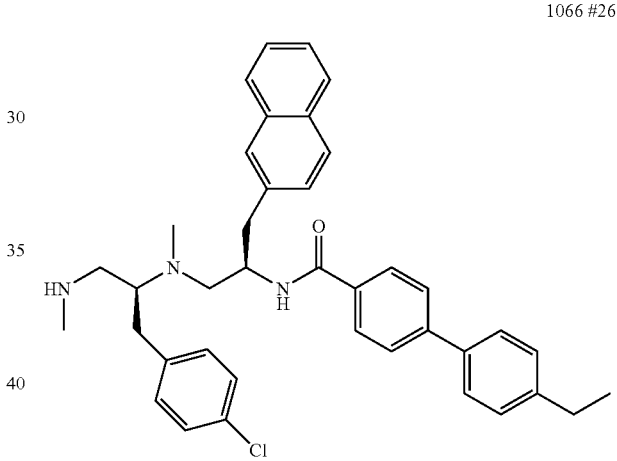

1066 #26

R1 = L-p-chloro-Phenylalanine
R2 = d-Naphthylalanine
R3 = 4-ethyl-4-biphenylcarboxylic acid From the acylamine libraries, we found that compounds bearing cyclic groups having hydroxy or hydroxy bearing substituents at position R3 were the most active inhibitors of biotinylated UEA-1 binding (Table 2) In case of the library TPI 1012, compounds with the following groups at positions R1, R2 and R3 showed the most activity.

D-Norleucine    L-Norleucine    D-Tyrosine

-continued

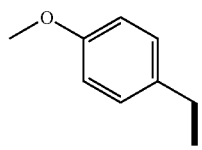

L-Tyrosine

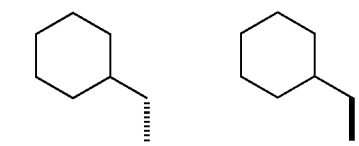

D-Cyclohexylalanine     L-Cyclohexylalanine

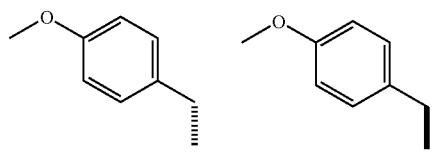

D-Tyrosine     L-Tyrosine

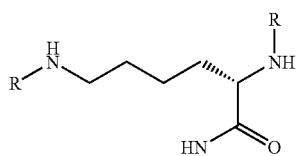

D-Arginine     L-Arginine

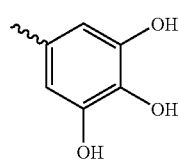

Gallic acid

In the light of these results, further libraries were synthesized using a range of carboxylic acids with the intention of assessing if multiple copies of polyhydroxyaryl groups such as galloyl groups and some other cyclic groups increased the inhibitory activity of the compounds. These compounds were synthesized on a lysine scaffold in which carboxylic acids were coupled to amines on both alpha and epsilon positions. Two different constructs with each carboxylic acid were made: a 'two copy' construct represented as formula (C) and a 'four copy' construct represented as formula (B).

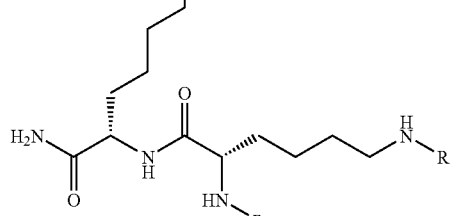

(B)

Four Copy Scaffold

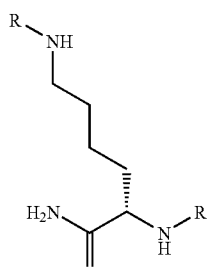

(C)

Two Copy Scaffold

A range of carboxylic acids were used to synthesize these two copy and four copy constructs. Structures of the acids attached to lysine scaffolds of this library are given below.

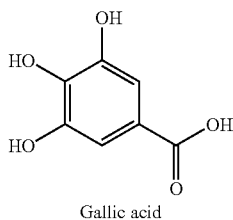

Gallic acid

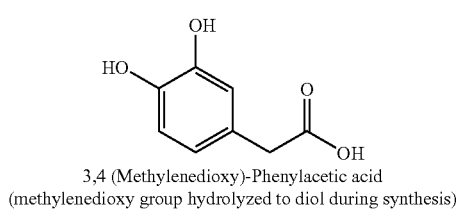

3,4 (Methylenedioxy)-Phenylacetic acid
(methylenedioxy group hydrolyzed to diol during synthesis)

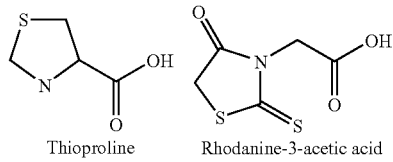

Thioproline    Rhodanine-3-acetic acid

By way of reference example, the reaction scheme for synthesis of compounds carrying four copies of gallic acid on a lysine scaffold is now described. The typical synthesis of such compounds involved solid phase organic chemistry methodology. This reaction scheme is illustrated in FIG. 1.

1. A quantity of 100 mg mBHA (methylbenzhydryl amine, sub. 0.8 mmol/g) derivatized polystyrene resin was contained within a polypropylene mesh packet called a "tea-bag". A mesh of this nature has previously been disclosed in Houghten, R. A., *Proc Nat Acad Sci.* USA. 1985, 82, 5131. The resin functionality, methyl benzhydrylamine, is the site of attachment for the first step in the synthesis. The mesh packet containing the resin was contained in a polyethylene bottle. The resin was washed three times with 5 ml methylene chloride and neutralized three times with 5 ml of 5% diisopropylethylamine/methylene chloride solution. Fmoc-D-Lysine(Boc)-OH (6 eq.) was then coupled (step 1 of FIG. 1) for two hours in the presence of HOBt (1-hydroxybenzotriazole, 6 eq.) and DIPCDI (diisopropylcarbodiimide, 6 eq.) in DMF (dimethylformamide) to afford compound A (FIG. 1). All reagents are utilized in six-fold excess to assure complete acylation. This mixture was shaken with the resin for two hours. The excess reagents were then washed out with DMF and methylene chloride.

2. The t-Boc protecting group was removed (Step 2 of FIG. 1) with 5 ml 55% trifluoroacetic acid/methylene chloride solution for 30 minutes. The resin was then washed with methylene chloride, isopropanol and again with methylene chloride.

3. The Fmoc group was then removed (Step 3 of FIG. 1) with a 5 ml solution of 20% piperidine in DMF for 30 minutes. Excess base was removed by washing three times with DMF.

4. The coupling procedure was repeated (Step 4 of FIG. 1) as described above to couple Fmoc-D-Lysine(Boc)-OH to both the α and ε amino positions producing compound B (FIG. 1).

5. Again, the t-Boc and Fmoc groups were removed (Steps 5 and 6).

6. The mesh packet and resin were next immersed in a solution of gallic acid (3,4,5-trihydroxybenzoic acid, 6 eq.), HOBt (6 eq.) and DIPCDI (6 eq.) in DMF.

7. The reaction mixture was shaken overnight (Step 7) All couplings were tested by the Kaiser test to verify completeness of the reaction.

8. Following the coupling of gallic acid, a treatment was necessary to remove esters that formed due to the phenolic nature of gallic acid. These esters were hydrolyzed in the final cleavage from the resin, however they remained as an undesired side product, complicating the post-synthesis purification process. The tea-bag was treated with a solution of 2 ml Hydrazine in 15 ml of 10%Methanol/90%Dioxane and shaken overnight (Step 8). The bag was finally washed with dioxane three times.

9. The compound was cleaved from the resin (Step 9) by hydrofluoric acid with 5% anisole as a scavenger. This reaction was kept at 0° C. for 90 minutes followed by a stream of nitrogen to remove excess HF. Following extraction with 95% acetic acid/5% water and lyophilization, the desired product C (FIG. 1) was obtained.

The biotinylated UEA-1 binding inhibitory activity of these compounds (Library N78) is shown in Table 4.

TABLE 4

INHIBITORY ACTIVITY OF INDIVIDUAL COMPOUNDS CONTAINING MULTIPLE COPIES OF CARBOXYLIC ACIDS.

| | | | | | | |
|---|---|---|---|---|---|---|
| Gallic acid | D-Lys | | 76.1 | 80.4 | 83.1 | 87.7 |
| Thioproline | D-Lys | Bis boc | −28.2 | −35.5 | −0.2 | −29.4 |
| 3,4-(Methylenedioxy)-Phenylacetic Acid | D-Lys | Bis boc | −6.2 | −15.3 | 26.6 | 36.3 |
| Rhodanine 3-acetic acid | D-Lys | Bis boc | −6 | 32.5 | 4.8 | 16.5 |
| Gallic Acid | D-Lys | Bis boc | 66.6 | 51.3 | 87 | 91 |
| Thioproline | D-Lys | Bis boc | −10.9 | −27.2 | 2.3 | 4.1 |

SD:- Standard Deviation
Av % Inhibition:- Average Percent Inhibition

As seen in Table 4, the polyhydroxyphenyl constructs were significantly more active than the individual monohydroxyphenyl compounds in inhibiting biotinylated UEA-1 binding to Caco-2 cell membranes. Then there was the question whether or not the presence or nature of the scaffolds upon which these groups were arranged contributed to the inhibitory activity of these compounds. In order to investigate this, firstly a range (library MSI 26) of commercially available compounds having aromatic groups with one or more hydroxy groups, such as gallic acid, and other related compounds were tested in the inhibition assays. The structures of compounds tested in this experiment (Table 5) are shown below.

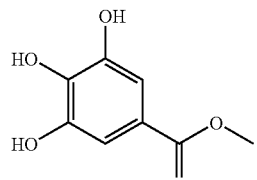

MSI 26 #1
Methyl 3,4,5-trihydroxybenzoate
Methyl Gallate

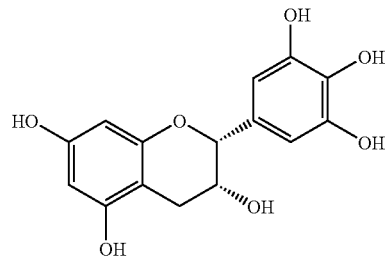

MSI26 #4
(-)-Epigallocatechin

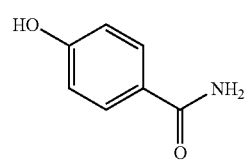

MSI 26#9
4-Hydroxybenzamide

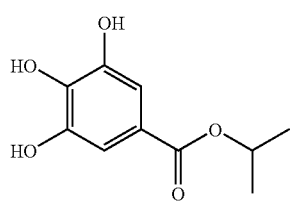

MSI26 #6
Isopropyl Gallate

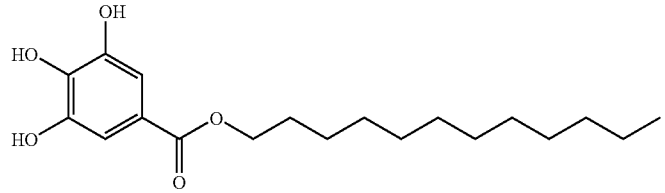

MSI26 #2
Lauryl Gallate

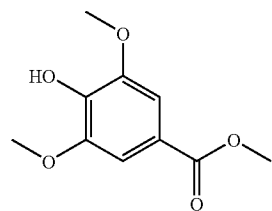

MSI 26 #8
Methyl Syringate

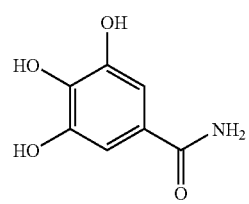

MSI26 #5
3,4,5-trihydroxybenzamide

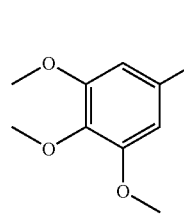

MSI 26 #7
Dilazep Dihydrochloride

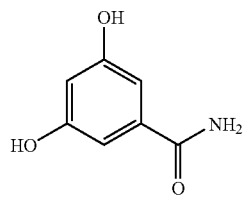

MSI 26 #10
3,5-Dihydroxybenzamide

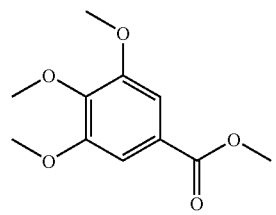

MSI 26 #11
Methyl 3,4,5-Trimethoxybenzoate

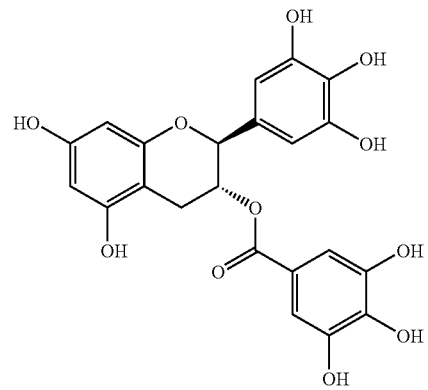

MSI26 #3
(-)-Gallocatechin Gallate

TABLE 5

| Library MSI 26 | Two Tier Assay Avg % Inhibition | | Single Tier Assay Avg % Inhibtion | |
|---|---|---|---|---|
| | 62.5 µg/ml | 250 µg/ml | 62.5 µg/ml | 250 µg/ml |
| Methyl 3,5,4-trihydroxybenzoate | −11 | −8 | 1 | 4.5 |
| Lauryl gallate | 20.4 | 47.9 | 39.1 | 22.5 |
| Gallocatechin gallate | 7 | 14.1 | 54.6 | 33.6 |
| Epigallocatechin | −12 | −10 | 10.1 | 0 |
| 3,4,5-trihydroxybenzamide | 10.7 | 41.4 | 41.7 | 21 |
| Isopropylgallate | −7 | 8.9 | 10.8 | 3.9 |
| Dilazep dihydrochloride | −25 | −25 | 14.7 | 10.4 |
| Methyl syringate | −10 | 0.2 | 17.4 | 8.4 |
| 4-hydroxybenzamide | −1 | 4.2 | −3 | 8.4 |
| 3,5-dihydroxybenzamide | −7 | −2 | −1 | 2.4 |
| 3,5-dihydroxybenzoic Acid | −5 | −7 | 0 | 1.1 |

Avg % Inhibition: - Average Percent Inhibition

As seen in Table 5, the rather low (although appreciable) inhibitory activity of the various polyhydroxyphenyl containing compounds suggested preferability of substantial molecular scaffolds in binding to the UEA-1 receptor. In addition, compounds with multiple polyhydroxyphenyl groups showed greater inhibitory activity. The results suggested the effect should be optimised by having multiple active side groups on scaffolds.

Therefore, a range of polyhydroxy aryl groups such as galloyl and other cyclic groups, as shown below, were attached to different lysine scaffolds.

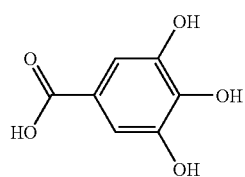

Gaillic Acid

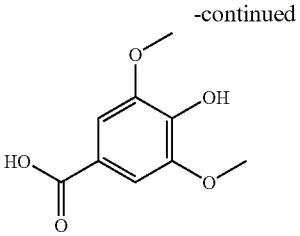

Syringic acid

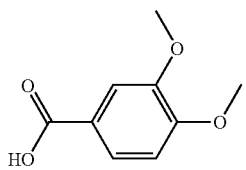

3,4-Dimethoxybenzoic acid

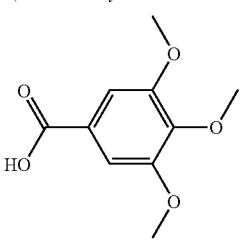

3,4,5-trimethoxybenzoic acid

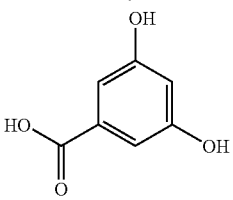

3,5-Dihydroxybenzoic acid

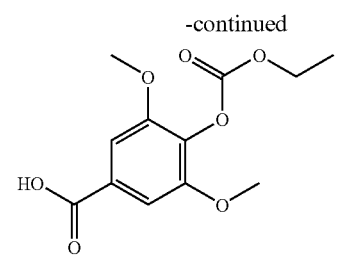

4-ethoxycarbonyl-3,5-dimethoxybenzoic acid

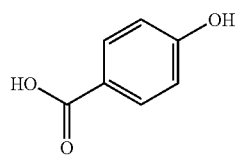

4-Hydroxybenzoic acid

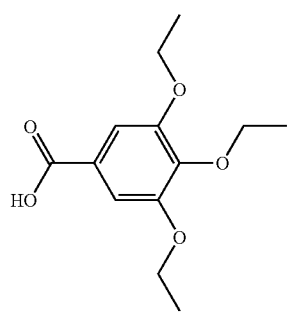

3,4,5-triethoxybenzoic acid

Both branched and linear skeletons as shown below were synthesized in this library which preferably contained up to four or more hydroxyl moieties. The resulting compounds (library MST 27) were tested in single and two tier assays the results of which are shown in Table 6.

Branched Structures

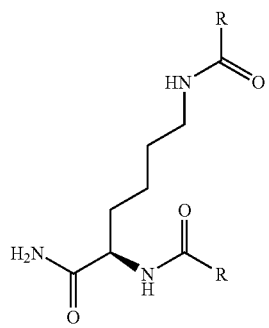

Two Copies

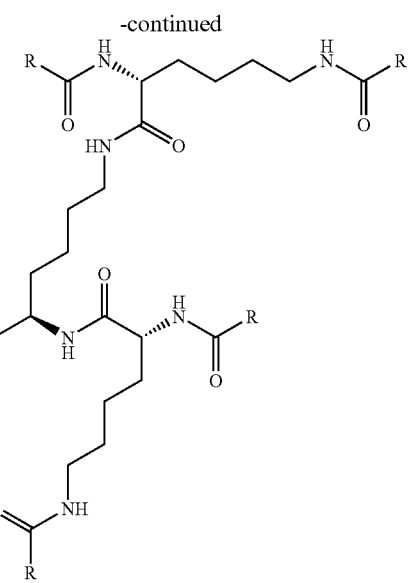

Linear Structures

Four Copies

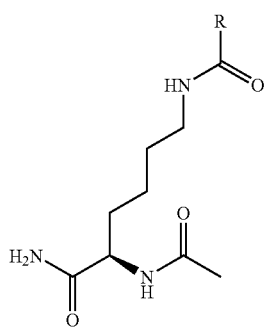

One Copy
N-Acetylated

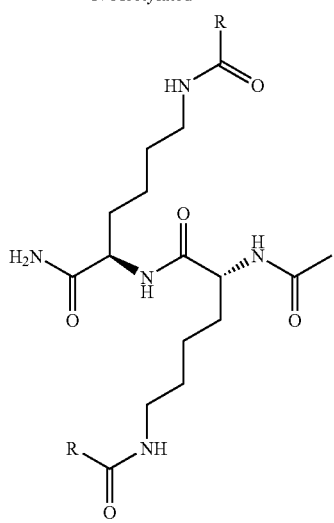

Two Copies
N-Acetylated

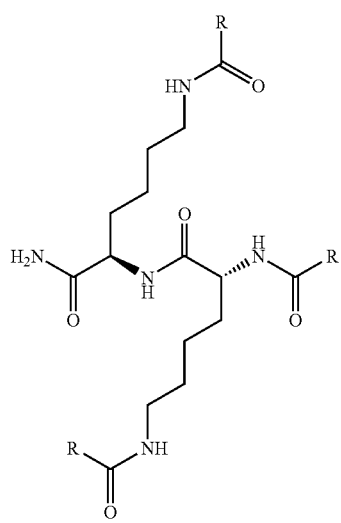

Three Copies

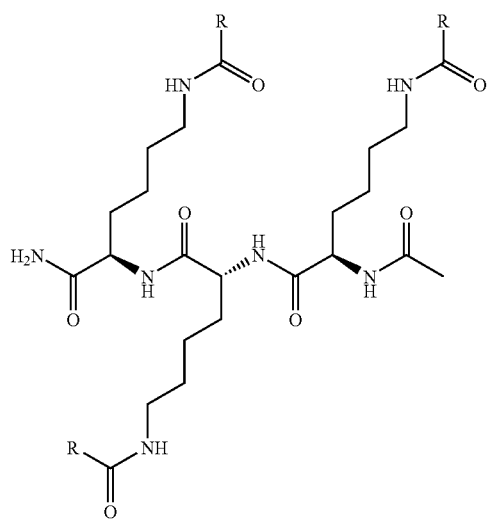

Three Copies
N-Acetylated

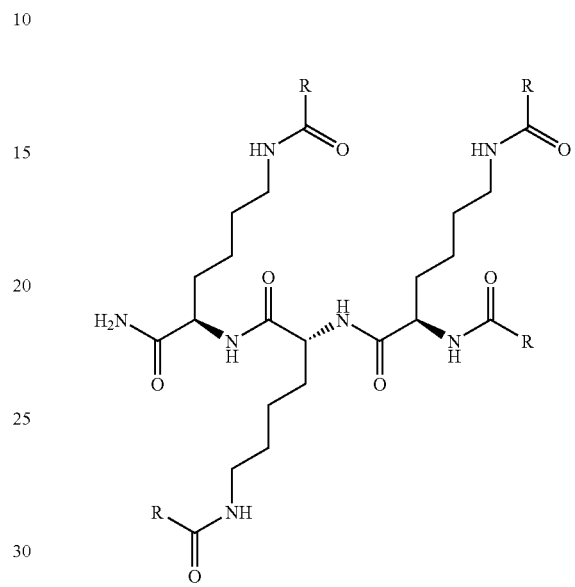

Four Copies

Analysis of the biotinylated UEA-1 binding inhibitory activity of these linear and branched compounds shows that the activity of the compounds increased with the increase in the number of gallic acid groups (structures of the active compounds are shown below).

Compounds with other carboxylic acids attached as side groups on the lysine scaffolds were not as active (Table 6).

TABLE 6

Inhibitory activity of lysine scaffolds both linear or branched with a variation of gallic acid constructs

| Cpd # | Library MSI 27 R | Comment | MW | Single Tier Assay IC50 (ug/ml) | uM | Two Tier Assay IC50 (ug/ml) | uM |
|---|---|---|---|---|---|---|---|
| 6 | Gallic acid | 2 copy structure | 449.41 | 18.97 | 42.21 | 12.97 | 28.86 |
| 2 | 3,4-Dimethoxybenzoic acid | 2 copy structure | 473.52 | 128.20 | 270.74 | 96.44 | 203.67 |
| 5 | 4-ethoxycarbonyl-3,5-dimethoxybenzoic acid | 2 copy structure | 505.52 | 168.10 | 332.53 | 130.70 | 258.55 |
| 1 | Syringic acid | 2 copy structure | 505.52 | 250.00 | 494.54 | 250.00 | 494.54 |
| 8 | 3,5-dihydroxybenzoic acid | 2 copy structure | 417.41 | 125.00 | 299.47 | 171.90 | 411.83 |
| 4 | 3,4,5-trimethoxybenzoic acid | 2 copy structure | 533.57 | 250.00 | 468.54 | 250.00 | 468.54 |
| 3 | 3,4,5-triethoxybenzoic acid | 2 copy structure | 617.72 | 250.00 | 404.71 | 250.00 | 404.71 |
| 7 | 4-Hydroxybenzoic acid | 2 copy structure | 385.41 | 250.00 | 648.66 | 250.00 | 648.66 |
| 13 | 4-ethoxycarbonyl-3,5-dimethoxybenzoic acid | 1 copy structure(N-term acetylated) | 367.40 | 89.92 | 244.75 | 73.30 | 199.51 |
| 14 | Gallic acid | 1 copy structure(N-term acetylated) | 339.35 | 129.70 | 382.20 | 91.52 | 269.69 |
| 15 | 4-Hydroxybenzoic acid | 1 copy structure(N-term acetylated) | 307.35 | 111.40 | 362.45 | 86.81 | 282.45 |
| 10 | 3,4-Dimethoxybenzoic acid | 1 copy structure(N-term acetylated) | 351.41 | 250.00 | 711.43 | 125.00 | 355.71 |
| 9 | Syringic acid | 1 copy structure(N-term acetylated) | 367.41 | 125.00 | 340.22 | 101.20 | 275.45 |
| 16 | 3,5-dihydroxybenzoic acid | 1 copy structure(N-term acetylated) | 323.35 | 250.00 | 773.16 | 108.30 | 334.93 |
| 11 | 3,4,5-triethoxybenzoic acid | 1 copy structure(N-term acetylated) | 423.51 | 250.00 | 590.31 | 250.00 | 590.31 |
| 12 | 3,4,5-trimethoxybenzoic acid | 1 copy structure(N-term acetylated) | 381.43 | 250.00 | 655.43 | 250.00 | 655.43 |
| 22 | Gallic acid | 4 copy structure | 1008.98 | 17.61 | 17.45 | 2.86 | 2.84 |
| 17 | Syringic acid | 4 copy structure | 1121.20 | 145.80 | 130.04 | 95.95 | 85.58 |
| 18 | 3,4-Dimethoxybenzoic acid | 4 copy structure | 1057.20 | 111.30 | 105.28 | 90.21 | 85.33 |
| 21 | 4-ethoxycarbonyl-3,5-dimethoxybenzoic acid | 4 copy structure | 1121.19 | 162.50 | 144.94 | 114.90 | 102.48 |
| 19 | 3,4,5-triethoxybenzoic acid | 4 copy structure | 1345.60 | 250.00 | 185.79 | 250.00 | 185.79 |
| 24 | 3,5-dihydroxybenzoic acid | 4 copy structure | 944.98 | 250.00 | 264.56 | 250.00 | 264.56 |
| 20 | 3,4,5-trimethoxybenzoic acid | 4 copy structure | 1177.30 | 250.00 | 212.35 | 250.00 | 212.35 |
| 23 | 4-Hydroxybenzoic acid | 4 copy structure | 880.98 | 250.00 | 283.77 | 250.00 | 283.77 |
| 30 | Gallic acid | Linear 3 copy structure | 729.69 | 25.89 | 35.48 | 8.36 | 11.45 |
| 26 | 3,4-Dimethoxybenzoic acid | Linear 3 copy structure | 765.86 | 125.00 | 163.22 | 85.62 | 111.80 |
| 29 | 4-ethoxycarbonyl-3,5-dimethoxybenzoic acid | Linear 3 copy structure | 813.85 | 111.50 | 137.00 | 93.43 | 114.80 |
| 27 | 3,4,5-triethoxybenzoic acid | Linear 3 copy structure | 982.16 | 250.00 | 254.54 | 250.00 | 254.54 |
| 25 | Syringic acid | Linear 3 copy structure | 813.86 | 250.00 | 307.18 | 250.00 | 307.18 |
| 28 | 3,4,5-trimethoxybenzoic acid | Linear 3 copy structure | 855.93 | 250.00 | 292.08 | 250.00 | 292.08 |
| 31 | 4-Hydroxybenzoic acid | Linear 3 copy structure | 633.69 | 250.00 | 394.51 | 250.00 | 394.51 |
| 32 | 3,5-dihydroxybenzoic acid | Linear 3 copy structure | 681.69 | 250.00 | 366.74 | 250.00 | 366.74 |
| 37 | 4-ethoxycarbonyl-3,5-dimethoxybenzoic acid | Linear 2 copy structure(N-term acetylated) | 675.73 | 82.46 | 122.03 | 54.27 | 80.31 |
| 38 | Gallic acid | Linear 2 copy structure(N-term acetylated) | 619.62 | 87.78 | 141.67 | 54.27 | 87.59 |
| 33 | Syringic acid | Linear 2 copy structure(N-term acetylated) | 675.73 | 97.85 | 144.81 | 72.17 | 106.80 |
| 34 | 3,4-Dimethoxybenzoic acid | Linear 2 copy structure(N-term acetylated) | 643.73 | 121.40 | 188.59 | 87.01 | 135.17 |
| 36 | 3,4,5-trimethoxybenzoic acid | Linear 2 copy structure(N-term acetylated) | 703.78 | 250.00 | 355.22 | 125.00 | 177.61 |
| 39 | 4-Hydroxybenzoic acid | Linear 2 copy structure(N-term acetylated) | 555.62 | 250.00 | 449.95 | 158.60 | 285.45 |
| 35 | 3,4,5-triethoxybenzoic acid | Linear 2 copy structure(N-term acetylated) | 787.93 | 250.00 | 317.29 | 250.00 | 317.29 |
| 40 | 3,5-dihydroxybenzoic acid | Linear 2 copy structure(N-term acetylated) | 587.62 | 250.00 | 425.45 | 250.00 | 425.45 |
| 46 | Gallic acid | Linear 4 copy structure | 1009.97 | 14.92 | 14.77 | 2.00 | 1.98 |
| 41 | Syringic acid | Linear 4 copy structure | 1122.19 | 89.77 | 80.00 | 83.26 | 74.19 |
| 42 | 3,4-Dimethoxybenzoic acid | Linear 4 copy structure | 1058.19 | 107.00 | 101.12 | 113.80 | 107.54 |
| 45 | 4-ethoxycarbonyl-3,5-dimethoxybenzoic acid | Linear 4 copy structure | 1122.18 | 154.20 | 137.41 | 136.30 | 121.46 |
| 43 | 3,4,5-triethoxybenzoic acid | Linear 4 copy structure | 1346.59 | 250.00 | 185.65 | 250.00 | 185.65 |
| 48 | 3,5-dihydroxybenzoic acid | Linear 4 copy structure | 945.97 | 250.00 | 264.28 | 250.00 | 264.28 |
| 44 | 3,4,5-trimethoxybenzoic acid | Linear 4 copy structure | 1178.29 | 250.00 | 212.17 | 250.00 | 212.17 |
| 47 | 4-Hydroxybenzoic acid | Linear 4 copy structure | 881.97 | 250.00 | 283.46 | 250.00 | 283.46 |
| 54 | Gallic acid | Linear 3 copy structure(N-term acetylated) | 899.90 | 6.85 | 7.61 | 3.00 | 3.33 |
| 50 | 3,4-Dimethoxybenzoic acid | Linear 3 copy structure(N-term acetylated) | 936.07 | 77.09 | 82.36 | 42.79 | 45.71 |
| 53 | 4-ethoxycarbonyl-3,5-dimethoxybenzoic acid | Linear 3 copy structure(N-term acetylated) | 1200.25 | 90.15 | 75.11 | 114.80 | 95.65 |
| 49 | Syringic acid | Linear 3 copy structure(N-term acetylated) | 984.07 | 118.00 | 119.91 | 108.80 | 110.56 |
| 56 | 3,5-dihydroxybenzoic acid | Linear 3 copy structure(N-term acetylated) | 851.90 | 125.00 | 146.73 | 125.00 | 146.73 |
| 52 | 3,4,5-trimethoxybenzoic acid | Linear 3 copy structure(N-term acetylated) | 1026.14 | 174.80 | 170.35 | 226.70 | 220.93 |
| 55 | 4-Hydroxybenzoic acid | Linear 3 copy structure(N-term acetylated) | 803.90 | 250.00 | 310.98 | 250.00 | 310.98 |
| 51 | 3,4,5-triethoxybenzoic acid | Linear 3 copy structure(N-term acetylated) | 1152.37 | 250.00 | 216.95 | 250.00 | 216.95 |

IC 50 = concentration of compound at which inhibition of binding is 50%

A second batch of the MSI 27 library of compounds was synthesized and the biotinylated UEA-1 binding inhibitory activity of compounds from the new batch (called MSI 40) was compared with their chemically identical counterparts from MSI 27. As shown in Tables 7(a) and 7(b), chemically identical compounds from both batches behaved in a similar manner. In addition, compounds from these libraries having gallic acid as their active binding moiety were compared with compounds where other carboxylic acids were attached as side groups on the lysine linear or branched scaffolds. As seen in Tables 7(a),(b) compounds having gallic acid as their side groups had low IC 50 values which suggested that the UEA-1 receptor binding inhibitory activity of these compounds was related to the specific gallic acid structure rather than being a general feature of carboxylic acids.

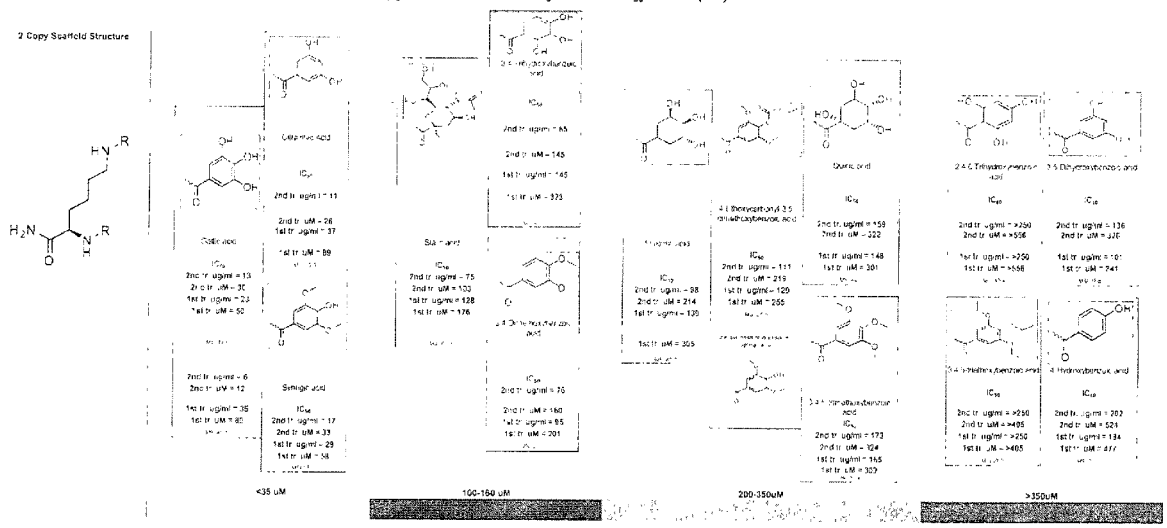

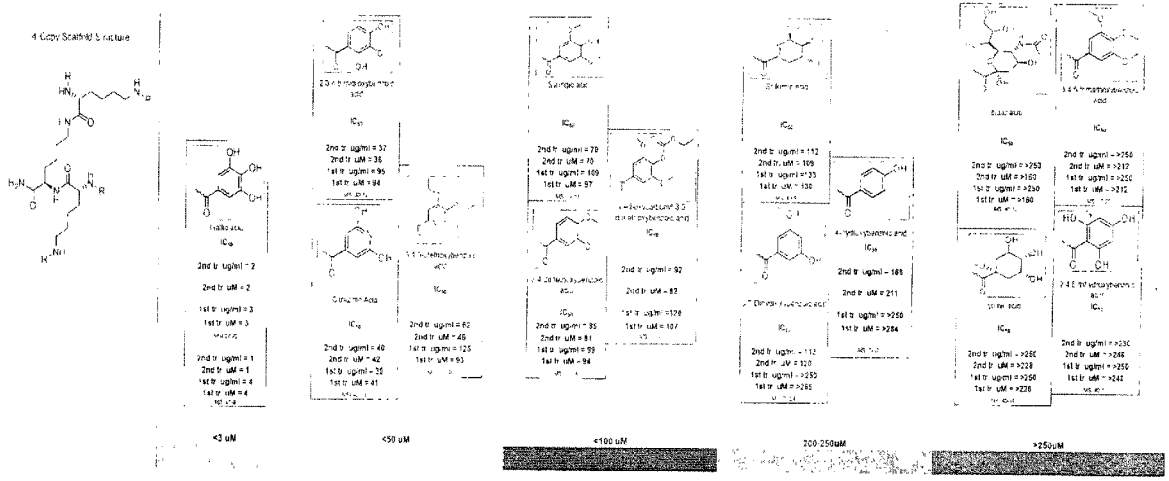

Structure of Most Active Compounds from MST 27
MSI 27 #6
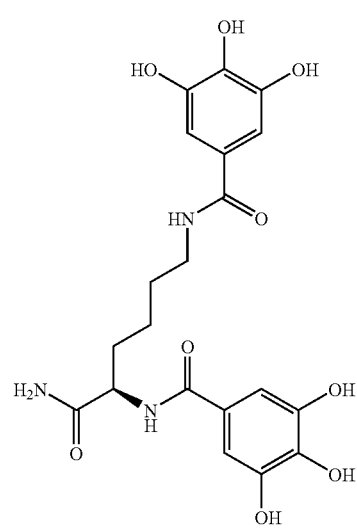
MSI 27#30
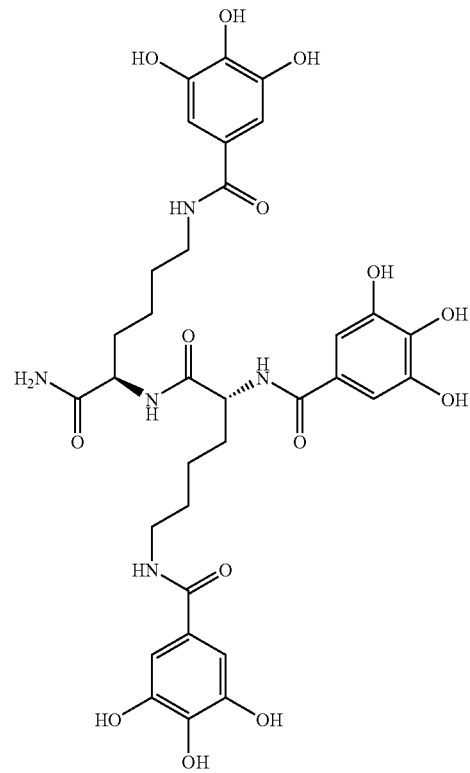
MSI 27#22
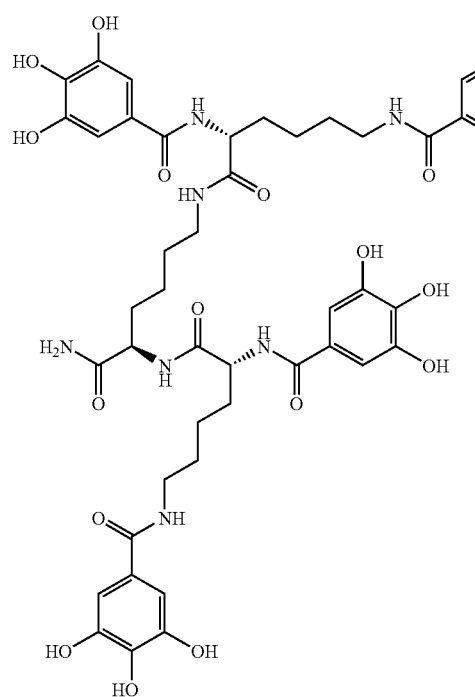
MSI 27#54
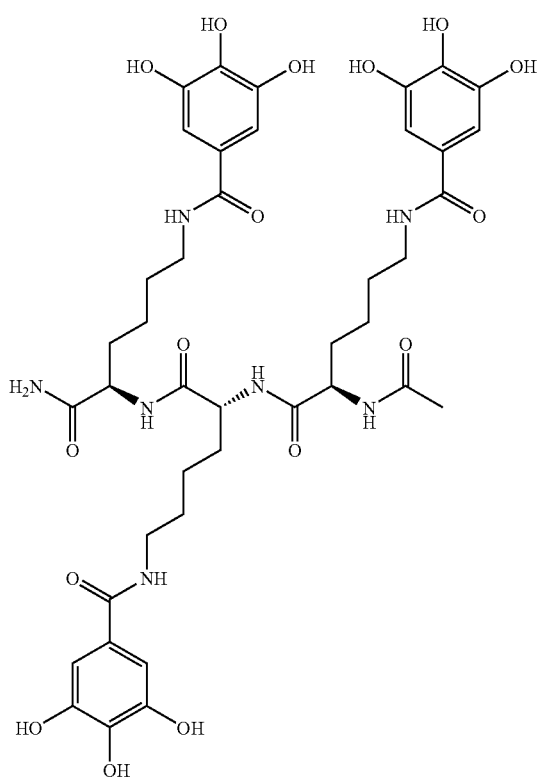

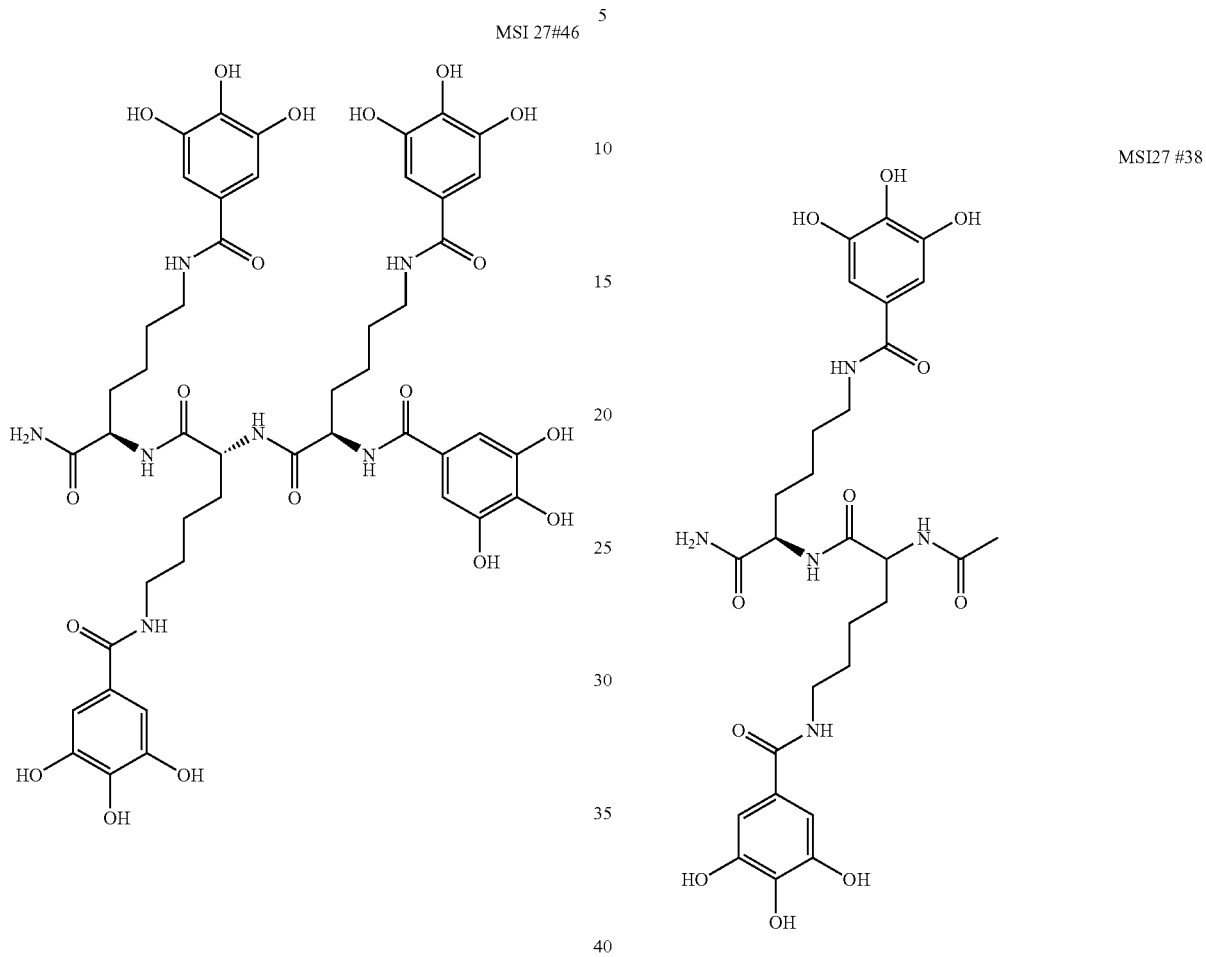

Structures of Less Active Components Containing Gallic Acid from MSI 27

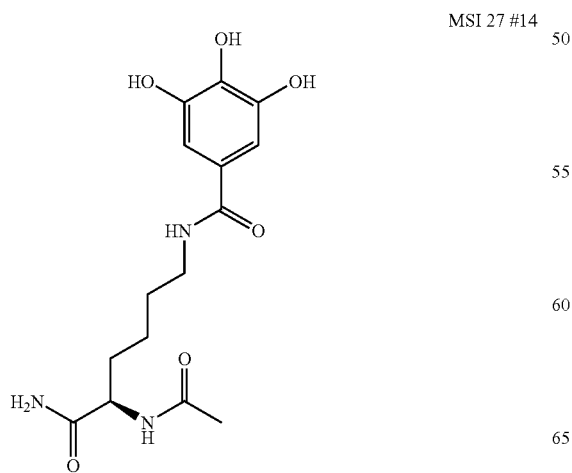

From these data, it appears that having more than one polyhydroxy aryl group contributes to good inhibition. Therefore, a range of such compounds was synthesized where up to eight—it could of course be more—galloyl polyhydroxy side groups were attached to lysine and other scaffolds, examples of which are shown below. The inhibitory activity of these compounds is shown in Table 8.

TABLE 8

| Structure | Synthesis Number | IC 50 (ug/ml) | IC 50 (uM) |
|---|---|---|---|
| One copy H Acetylated | MSI 27 #14 | 1st tier = 72<br>2nd tier = 211 | 1st tier = 54<br>2nd tier = 160 |
| Two copy branched | MSI 27 #6<br>MSI 40 #1 | 1st tier = 11<br>2nd tier = 8 | 1st tier = 24<br>2nd tier = 17 |
| Two copy DAP | MSI 34 #1<br>MSI 39 #1 | 1st tier = 1<br>2nd tier = 0.8 | 1st tier = 4<br>2nd tier = 2 |
| Two copy DAB | MSI 34 #2<br>MSI 39 #5 | 1st tier = 3<br>2nd tier = 2 | 1st tier = 6<br>2nd tier = 5 |

TABLE 8-continued

| Structure | Synthesis Number | IC 50 (ug/ml) | IC 50 (uM) |
|---|---|---|---|
| Two copy Orn | MSI 34 #3 | 1st tier = 2<br>2nd tier = 0.7 | 1st tier = 4<br>2nd tier = 2 |
| Two copy Phe (p-HN2) | MST 34 #4 | 1st tier = 17<br>2nd tier = 18 | 1st tier = 35<br>2nd tier = 37 |
| Two copy N-Acetylated | MSI 27 #38 | 1st tier = 54<br>2nd tier = 48 | 1st tier = 86<br>2nd tier = 77 |

TABLE 8-continued
| Structure | | Synthesis Number | IC 50 (ug/ml) | IC 50 (uM) |
|---|---|---|---|---|
| Three copy linear | 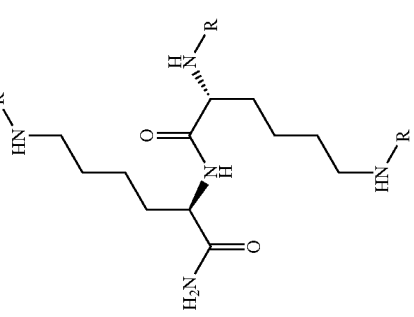 | MSI 27 #30<br>MSI 39 #9 | 1st tier = 14<br>2nd tier = 5 | 1st tier = 19<br>2nd tier = 7 |
| Three copy linear DAP | 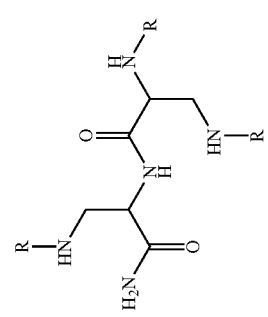 | MSI 34 #9 | 1st tier = 0.6<br>2nd tier = 0.5 | 1st tier = 0.9<br>2nd tier = 0.8 |
| Three copy linear DAB | 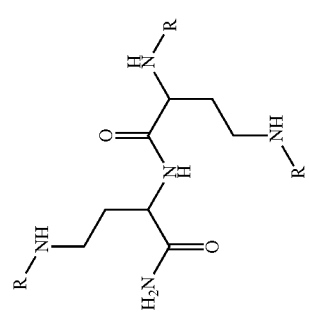 | MSI 34 #10 | 1st tier = 0.6<br>2nd tier = 0.7 | 1st tier = 0.9<br>2nd tier = 1 |

TABLE 8-continued
| Structure | Synthesis Number | IC 50 (ug/ml) | IC 50 (uM) |
|---|---|---|---|
| Three copy linear Orn 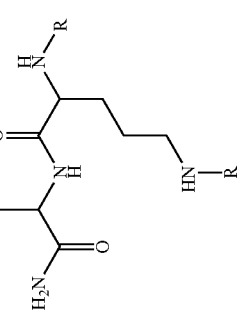 | MSI 34 #11 | 1st tier = 1<br>2nd tier = 0.8 | 1st tier = 2<br>2nd tier = 1 |
| Three copy linear Phe(p-NH2) 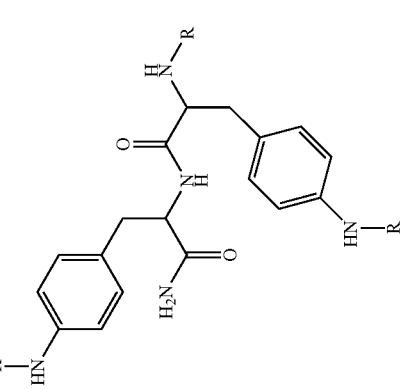 | MSI 34 #12 | 1st tier = 6<br>2nd tier = 4 | 1st tier = 8<br>2nd tier = 5 |

TABLE 8-continued

| Structure | Synthesis Number | IC 50 (ug/ml) | IC 50 (uM) |
|---|---|---|---|
| Three copy N-Acetylated | MSI 27 #54<br>MSI 39 #10 | 1st tier = 4<br>2nd tier = 2 | 1st tier = 5<br>2nd tier = 3 |
| Three copy N—Ac DAP | MSI 34 #13 | 1st tier = 2<br>2nd tier = 2 | 1st tier = 3<br>2nd tier = 2 |
| Three copy N—Ac DAB | MSI 34 #14 | 1st tier = 2<br>2nd tier = 1 | 1st tier = 2<br>2nd tier = 1 |

TABLE 8-continued
| Structure | Synthesis Number | IC 50 (ug/ml) | IC 50 (uM) |
|---|---|---|---|
| Three copy N—Ac Orn 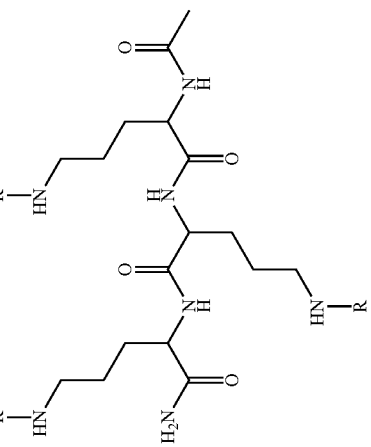 | MSI 34 #15 | 1st tier = 8<br>2nd tier = 2 | 1st tier = 9<br>2nd tier = 2 |
| Three copy N—Ac Phe(p-NH2) 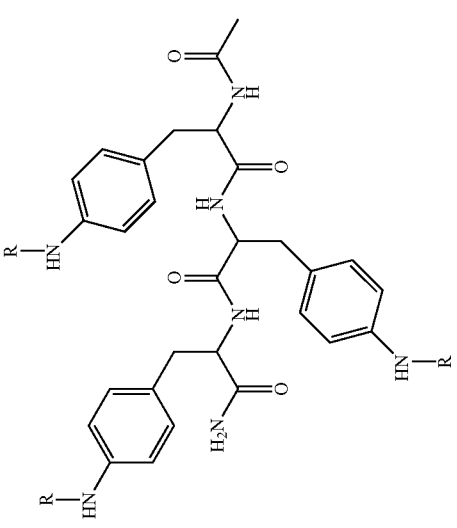 | MSI 34 #16 | 1st tier = 3<br>2nd tier = 6 | 1st tier = 3<br>2nd tier = 6 |

TABLE 8-continued
| Structure | | Synthesis Number | IC 50 (ug/ml) | IC 50 (uM) |
|---|---|---|---|---|
| Four copy branched | 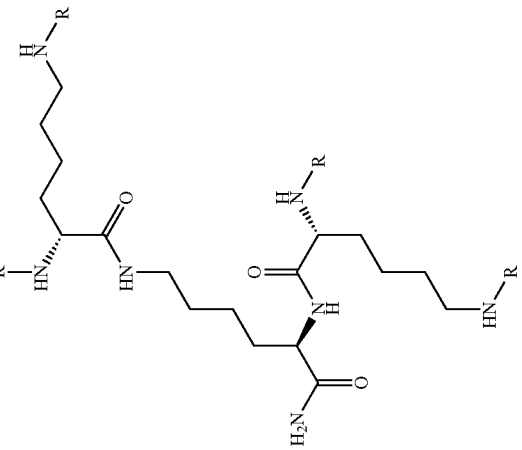 | MSI 27 #22<br>MSI #8 | 1st tier = 10<br>2nd tier = 1 | 1st tier = 10<br>2nd tier = 1 |
| Four copy DAP | 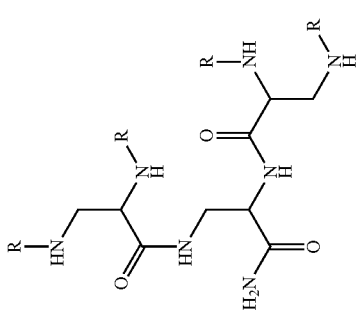 | MSI 34 1π5 | 1st tier = 0.5<br>2nd tier = 1 | 1st tier = 0.5<br>2nd tier = 1 |

TABLE 8-continued
| | Structure | Synthesis Number | IC 50 (ug/ml) | IC 50 (uM) |
|---|---|---|---|---|
| Two-by-Two DAP with linker | 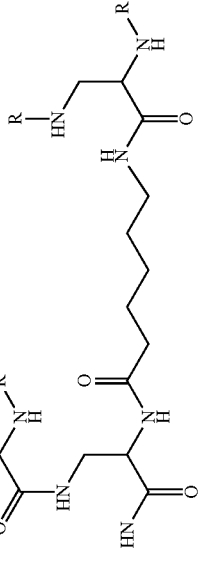 | MSI 39 #4 | 1st tier = 6<br>2nd tier = 0.8 | 1st tier = 5<br>2nd tier = 0.7 |
| Four copy DAB | 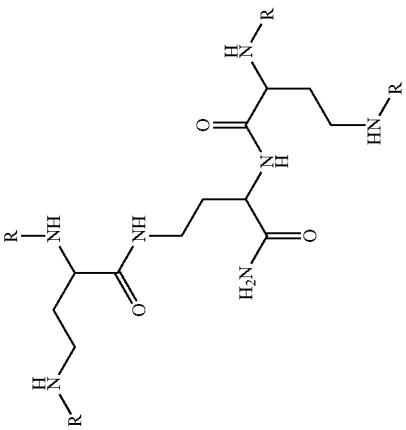 | MSI 34 #6 | 1st tier = 0.6<br>2nd tier = 1 | 1st tier = 0.6<br>2nd tier = 1 |

TABLE 8-continued
| Structure | Synthesis Number | IC 50 (ug/ml) | IC 50 (uM) |
|---|---|---|---|
| Four copy Orn | MSI 34 #7 | 1st tier = 0.9<br>2nd tier = 1 | 1st tier = 0.9<br>2nd tier = 1 |
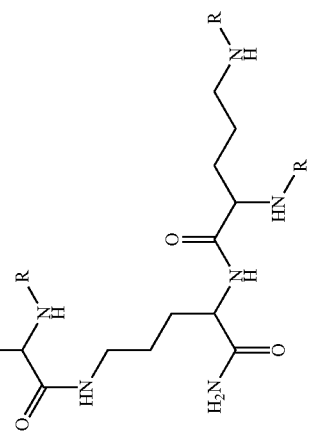

TABLE 8-continued
| Structure | Synthesis Number | IC 50 (ug/ml) | IC 50 (uM) |
|---|---|---|---|
| Four copy Phe(p-NH2) | MSI 34 #8 | 1st tier = 4<br>2nd tier = 3 | 1st tier = 4<br>2nd tier = 2 |
| Four copy linear | MSI 27 #46<br>MSI 39 #11 | 1st tier = 8<br>2nd tier = 0.6 | 1st tier = 8<br>2nd tier = 0.6 |
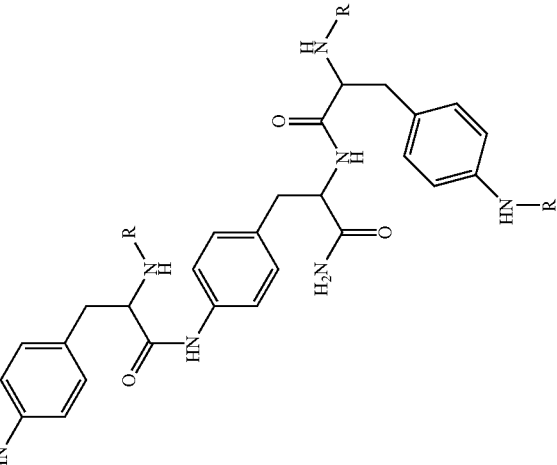
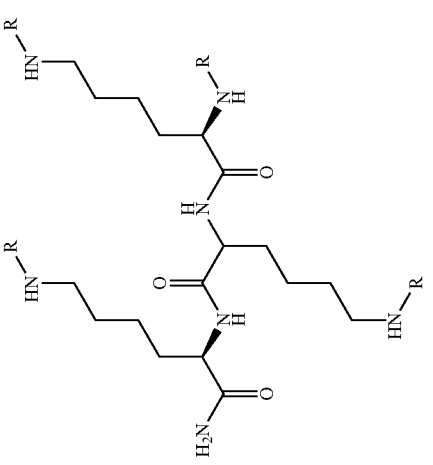

TABLE 8-continued

| | Structure | Synthesis Number | IC 50 (ug/ml) | IC 50 (uM) |
|---|---|---|---|---|
| Four copy linear DAP | 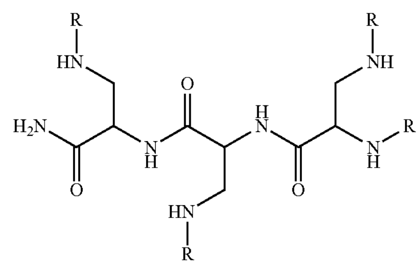 | MSI 34 #17 | 1st tier = 1<br>2nd tier = 0.7 | 1st tier = 1<br>2nd tier = 0.8 |
| Four copy linear DAB | 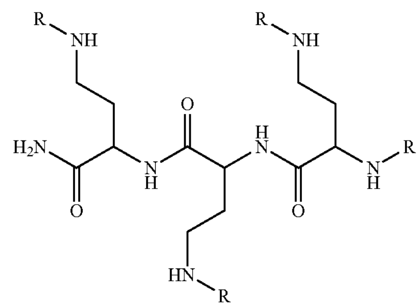 | MSI 34 #18 | 1st tier = 3<br>2nd tier = 0.9 | 1st tier = 3<br>2nd tier = 1 |
| Four copy linear Orn | 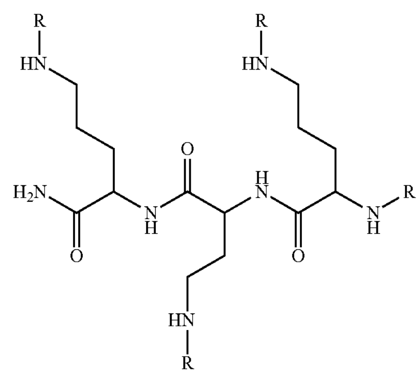 | MSI 34 #19 | 1st tier = 11<br>2nd tier = 1 | 1st tier = 11<br>2nd tier = 1 |

TABLE 8-continued

| Structure | Synthesis Number | IC 50 (ug/ml) | IC 50 (uM) |
|---|---|---|---|
| Four copy linear Phe(p-NH2) | MSI 34 #20 | 1st tier = 2<br>2nd tier = 6 | 1st tier = 2<br>2nd tier = 5 |
| Four copy N-Acetylated | MSI 30 #5<br>MSI 39 #12 | 1st tier = 8<br>2nd tier = 3 | 1st tier = 7<br>2nd tier = 2 |

TABLE 8-continued

| Structure | Synthesis Number | IC 50 (ug/ml) | IC 50 (uM) |
|---|---|---|---|
| Four copy N—Ac DAP | MSI 34 #21 | 1st tier = 2<br>2nd tier = 1 | 1st tier = 2<br>2nd tier = 1 |
| Four copy N—Ac DAB | MSI 34 #22 | 1st tier = 3<br>2nd tier = 1 | 1st tier = 3<br>2nd tier = 1 |
| Four copy N—Ac Orn | MSI 34 #23 | 1st tier = 6<br>2nd tier = 1 | 1st tier = 5<br>2nd tier = 1 |

TABLE 8-continued

| Structure | Synthesis Number | IC 50 (ug/ml) | IC 50 (uM) |
|---|---|---|---|
| Four copy N—Ac Phe(p-NH2) | MSI 34 #24 | 1st tier = 3<br>2nd tier = 9 | 1st tier = 2<br>2nd tier = 7 |
| Five copy linear | MSI 30 #5 | 1st tier = 75<br>2nd tier = 12 | 1st tier = 64<br>2nd tier = 10 |

TABLE 8-continued

| Structure | Synthesis Number | IC 50 (ug/ml) | IC 50 (uM) |
|---|---|---|---|
| Five copy N-Acetylated | MSI 30 #8 | 1st tier = 70<br>2nd tier = 15 | 1st tier = 48<br>2nd tier = 10 |
| Six copy linear | MSI 30 #10 | 1st tier = 23<br>2nd tier = 5 | 1st tier = 14<br>2nd tier = 3 |

TABLE 8-continued

| Structure | Synthesis Number | IC 50 (ug/ml) | IC 50 (uM) |
|---|---|---|---|
| Six copy N-Acetylated | MSI 30 #11 | 1st tier = 13<br>2nd tier = 2 | 1st tier = 7<br>2nd tier = 1 |
| Seven copy linear | MSI 30 #13 | 1st tier = 9<br>2nd tier = 3 | 1st tier = 5<br>2nd tier = 1 |

TABLE 8-continued
| Structure | Synthesis Number | IC 50 (ug/ml) | IC 50 (uM) |
|---|---|---|---|
| Seven copy N-Acetylated 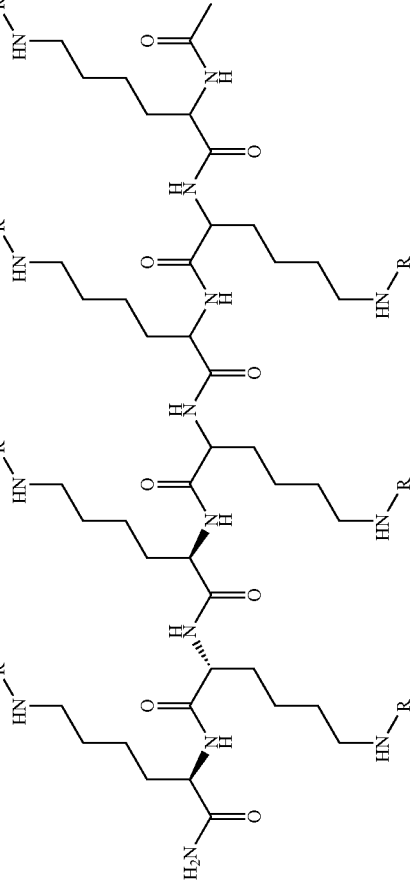 | MSI 30 #14 | 1st tier = 17<br>2nd tier = 9 | 1st tier = 8<br>2nd tier = 4 |
| Eight copy linear 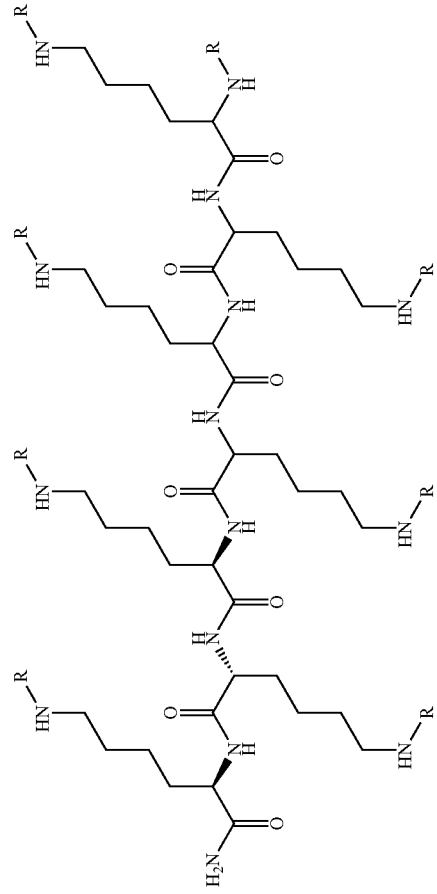 | MSI 30 #16 | 1st tier = 19<br>2nd tier = 8 | 1st tier = 9<br>2nd tier = 4 |

TABLE 8-continued

| | Structure | Synthesis Number | IC 50 (ug/ml) | IC 50 (uM) |
|---|---|---|---|---|
| Eight copy branched | 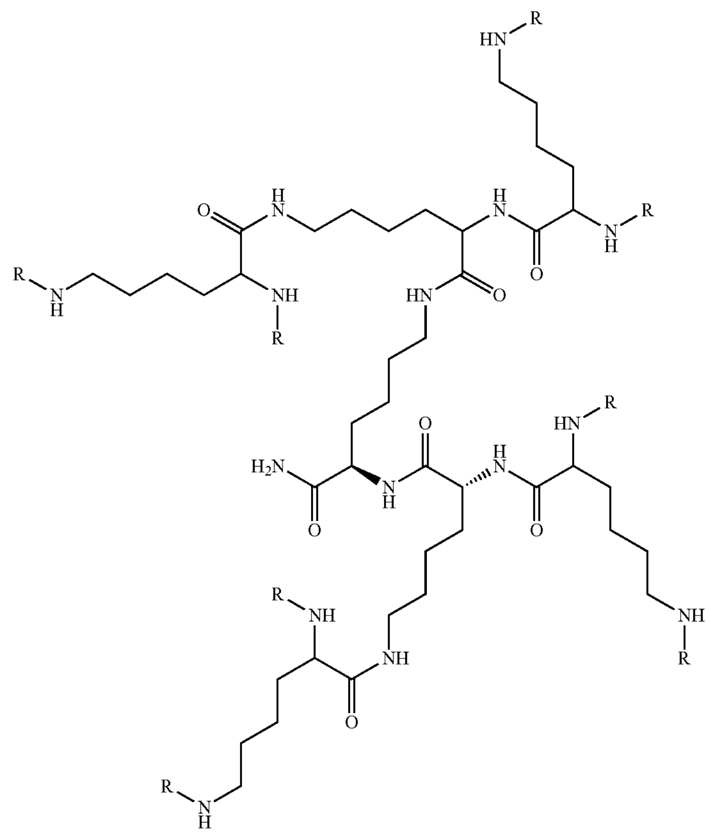 | MSI 30 #17 | 1st tier = 5<br>2nd tier = 5 | 1st tier = 2<br>2nd tier = 2 |

Note:
The Lysine scaffolds are synthesized from Fmoc-D-Lys(Boc)-OH whereas other scaffolds (DAP, DAB etc) are synthesized from the L derivatives.
R = 3,4,5-trihydroxybenzoyl Pharmaceutical Formulations As regards the kinds of pharmaceutical formulations to which the invention relates, it will be understood from the above that they may in general be any kind of formulation which is to be applied to the body's epithelium, but more particularly will generally be enteric formulations and most preferably oral formulations. Typically these consist of or comprise solids, such as capsules, tablets, powders, emulsions, such as microemulsions and other types thereof and suspensions. Preferred embodiments include controlled release oral formulations, in which the pharmaceutically-active ingredient is encapsulated in a biodegradable polymeric body or coating, e.g. by means of a solvent evaporation method. Coatings of this kind are known in the art, for example the polylactide polymer coatings discussed in our WO-A-00/12124 and elsewhere. There is no particular limit on the type of biodegradable polymer that may be used.

The encapsulated pharmaceutically-active material is preferably in the form of small particles, particularly microparticles or nanoparticles. For example, it may be a particulate formulation in which at least 50% of the particles are smaller than 5 µm, or more preferably in which as least 50% of the particles are smaller than 600 nm. Microparticulate and nanoparticulate compositions of this type, comprising drug-active material encapsulated in biodegradable polymer, are known as such to the skilled person: see e.g. WO-A-00/12124 and WO-A-96/31202.

The present ligand compound may be bound to, coated onto or blended with the drug formulation in any appropriate manner using physical and chemical techniques appropriate to the compounds concerned. Typically these consist of, but are not limited to, passive adsorption, direct conjugation during one step synthesis (e.g. ligand-peptide drug synthesis on standard columns or in solution), covalent coupling (e.g. amino group of ligand to carboxylate modified drug or delivery system using standard methodologies such as carbodiimide), and biotin-streptavidin interaction (e.g. using biotinylated ligand and streptavidin modified drug or delivery system).

As is also known practice, the particulate formulation may be given an "enteric coating" to protect it against gastric fluids so that the particles can pass intact into the intestine.

Development of a Whole Cell Binding Assay for the Characterization of Binding Affinities of the Lectin Mimetics:

A whole cell binding assay was developed for the characterization of binding affinities of various lectin mimetics of UEA-1. This assay was developed to allow structure activity analysis of these UEA-1 mimetics in order to identify functional groups that enhance activity using whole cells in solution.

Methods:

Caco-2 cells were analysed by flow cytometry for binding of both biotinylated UEA-1 and a biotinylated lectin mimetic of UEA-1 using a streptavidin FITC probe. While clear binding (positives) of biotinylated UEA-1 at concentrations as low as 1.0 µg/ml was seen, binding of the lectin mimetics of UEA-1 was negative even at concentrations of up to 65 μM. In order to amplify the signal, a FITC-avidin D sandwich protocol was used. In this method, after binding of the biotinylated compounds to the cells, a series of FITC-avidin D/anti-avidin D/FITC-avidin D stainings were performed, which resulted in a several fold increase in fluorescent signal.

Results:

The sandwich protocol described above increased the fluorescent signal as evidenced by the ability to measure a biotinylated UEA-1 sample of 0.02 μg/ml. Previously, the lower limit had been 1.0 μg/ml with the streptavidin-FITC probe. The nucleic acid stain 7-actinomycin D (7-AAD), a fluorescent dye for dead cells, was used to exclude these cells from analysis as they were known to bind non specifically to FITC-avidin D. Binding of biotinylated lectin mimetics of UEA-1 was demonstrated at both 50 μm and 10 μm concentrations.

Approximately, 15% of the population of Caco-2 cells tested were FL1 (FTTC) positive, FL3(7-AAD)negative at both concentrations after subtraction of background fluorescence. The streptavidin FITC stain was unable to detect these concentrations of the compound.

Conclusion:

A whole cell binding assay has been developed for the characterization of binding affinities of small molecule lectin mimetics of UEA-1. This will allow structure activity analysis of these mimetics to identify those functional groups that enhance activity using whole cells in solution. This assay will aid selection of small molecule mimics of UEA1 for further studies in vivo and is an independent novel aspect herein.

Evaluation of the Ability of Gallic Acid UEA 1 Mimetic Compounds to Mediate Delivery of a Model Particle System In Vivo:

The ability of compounds having gallic acid side chains to mimic UEA-1 was assessed in vivo in mouse models. Here, binding and uptake by M cells of particles coated with these compounds was assessed.

Methods:

Biotinylated ligand MSI 35-2 (4 copies of gallic acid; lysine scaffold) (see FIG. 5), a UEA-1 control (Vector Laboratories) and a biocytin control (Molecular Probes) were adsorbed on to fluorescent Estapor streptavidin polystyrene particles (FITC label; 0.289 μm diameter) using routine methodologies at room temperature.

Mouse intestinal loops containing one or more Peyer's Patches were inoculated with polystyrene particle suspensions (typically 500 μl containing $5.0\times10^{10}$ particles per ml) and incubated for 30 min. The Peyer's patches were excised, fixed in methanol and the M cells were counter-stained with UEA1-rhodamine for subsequent analysis by confocal microscopy. Stained tissues were examined on a BioRad MRC 600 confocal laser scanning microscope equipped with an argon/krypton mixed gas laser. The number of particles observed per total area was measured and reported quantitatively. For details of typical procedures and full protocols see: Foster, N., Clark, M. A., Jepson, M. A. & Hirst, B. H. Ulex europaeus 1 lectin targets microspheres to mouse Peyer's patch M-cells in vivo. Vaccine 1998:16(5); 536–541.

Results:

Scatter plots (log scale) for binding and uptake of MSI35-2, UEA1 and control coated particles are illustrated as FIGS. 2–4.

FIG. 2 Surface binding and uptake of MSI35-2 gallic acid mimetic coated particles.

FIG. 3 Surface binding and uptake of UEA1 coated particles.

FIG. 4 Surface binding & uptake of biocytin mimetic coated particles.

Each point on the scatter plot represents one image.

Conclusions:

Fluorescent streptavidin polystyrene particles coated with the biotinylated ligand MSI35-2 (4 copies of gallic acid; lysine scaffold) exhibited binding and uptake into M-cells in vivo comparable to or greater than UEA-1 coated control particles in a mouse intestinal loop model. Binding and uptake into M-cells was significantly higher than that observed using biocytin coated control particles.

The potential for use of these lectin mimetics in oral targeted drug delivery applications has been demonstrated using a model particulate system. The M-cell specific nature of the mimetic in the mouse intestinal loop model is of particular interest in the context of vaccine delivery to antigen presenting cells.

Staining of Human Tissue Sections with UEA-1:

The application of UEA-1 as a diagnostic/prognostic indicator of disease states was verified in human tissues.

Methods:

I. Immunohistochemistry Procedure

Using UEA1 @ 0.25 µg/ml, goat anti-UEA1 @ 1:10,000 dilution and a Vector ABC-AP Kit (AK5002) with a Vector Red substrate kit (SK-5100) microscopic analysis of human tissue sections revealed a fuchsia-colored red deposit at the site of ligand binding. Negative controls, performed in the absence of the primary ligand prior to application of the goat anti-UEA1 antibody and detection staining, revealed negligible background. Tissues stained with a positive control antibody (i.e. CD31; to ensure that the tissue antigens were preserved and accessible for immunohistochemical analysis) confirmed tissue integrity.

II. Tissue Sources and Diagnoses

| Tissue | Diagnosis | Sample ID | Age/Sex |
|---|---|---|---|
| Ileum | Normal, with Peyer's patches | 1 | 68 F |
| Ileum | Normal, with Peyer's patches | 2 | 36 F |
| Colon | Normal | 1 | 26 M |
| Colon | Normal | 2 | 73 F |
| Colon | Carcinoma | 1 | Adult |
| Colon | Carcinoma | 2 | Adult |
| Colon | Crohn's disease | 1 | 25 M |
| Colon | Crohn's disease | 2 | 31 M |
| Colon | Ulcerative colitis | 1 | Adult |
| Colon | Ulcerative colitis | 2 | 54 M |

Figure 6:
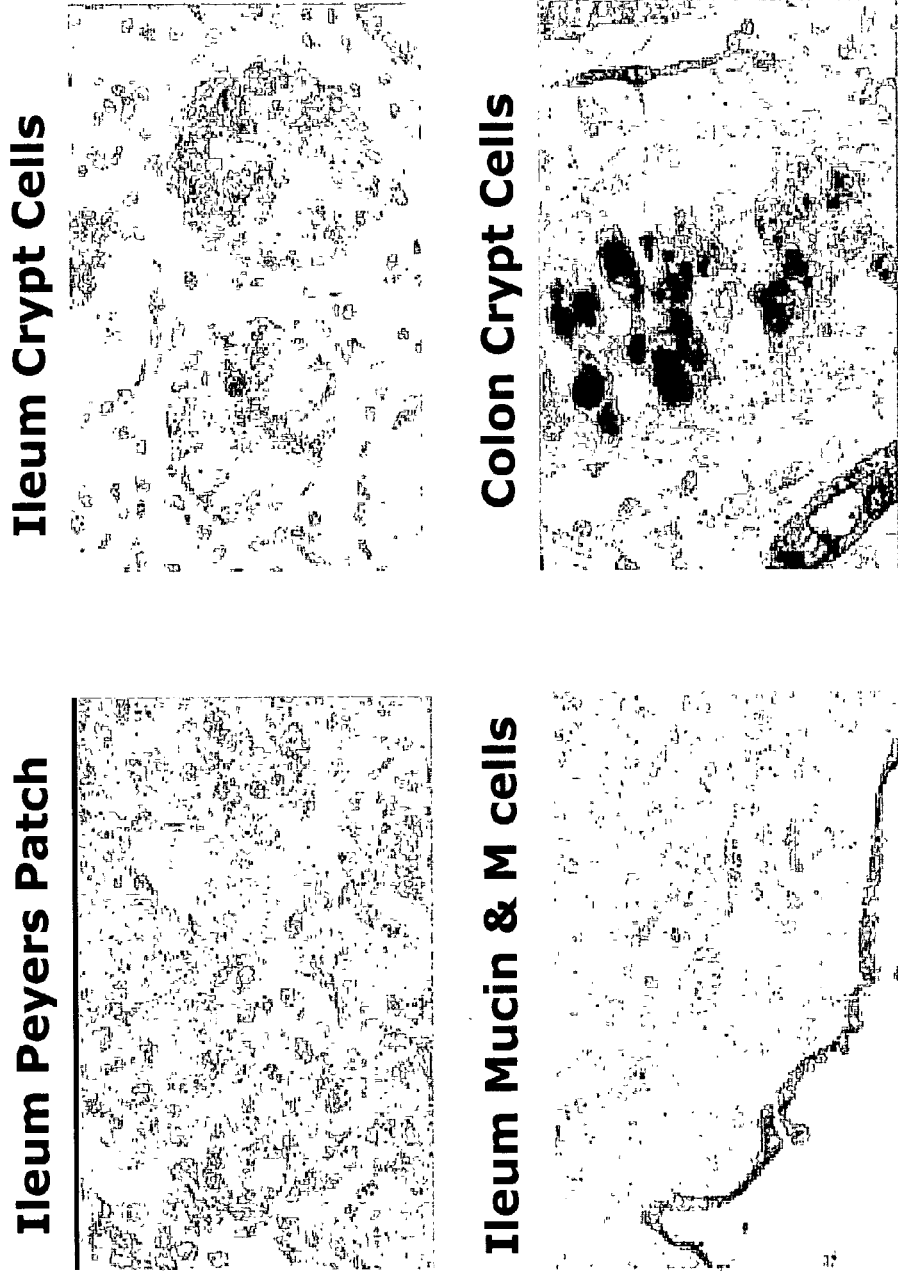

Results:

FIGS. 6, 7 show images of the stained cell samples. In the normal tissue, both the ileum and colon mucosal epithelia showed moderately positive cytoplasmic labeling of the absorptive, goblet, M-cell, and crypt enterocytes with UEA1. The staining reaction was slightly more pronounced in the colon than in the ileum and appeared strongest within cytoplasmic vacuoles, especially along the microvillus luminal surface of the mucosal cells. The stained material was secreted into the mucous that lines the intervillous and surface mucosal cells. Cell membranes and/or glycocalyx were stained, while the intercellular junctions were not demonstrated by the staining of the ligand binding sites. Goblet cells in both samples showed staining of fine dust-like to punctate cytoplasmic vesicles, and almost all goblet cells had strong staining of globular proteinaceous masses within the large cytoplasmic mucous vacuole. The staining indicated that the ligand binds to a specific component in the mucous or at the apical-mucous interface on the apical surface and not mucous in general, because some of the goblet cells, which contained mucous, did not stain. Several macrophages were positive with what appeared to be phagocytized debris.

Throughout the stroma of the normal and diseased ileum and colon and the colon carcinoma, there was a moderate to marked staining of all of the endothelial cells, and a minimal to moderate staining of the Schwann cells surrounding nerve axons. The Meissner's plexus and myenteric plexus and their axons were consistently positive.

In the colon carcinoma samples the intensity of staining was similar to that of normal colon. However, the pattern was somewhat different. In the colon carcinoma sections the foci of cytoplasmic staining tended to be smaller and of more uniform size and cytoplasmic distribution. In the normal tissue the reactivity was marked in the goblet cells, whereas in the carcinoma tissue goblet cells were less common and did not stain as intensely. In the colon sections, the staining reactivity grade was similar to that of the normal samples, but it was noticeably higher than that in the adjacent normal colon tissue in the same sample as the evaluated neoplastic tissue.

The immunohistological evaluation of inflammatory bowel disease with the ligand consisted of staining two cases each of Crohn's disease and ulcerative colitis. The expression of UEA1 receptors appeared to be significantly up-regulated in all of the mucosal enterocyte types in Crohn's disease, and appeared to be significantly down-regulated in ulcerative colitis in all of the colonic mucosal enterocytes.

Conclusions:

This difference in intensity of UEA-1 staining and/or patterning of the staining as between normal and afflicted cells provides a basis for a diagnosis or prognosis in the present techniques.

Further Staining of Human Tissue Sections with UEA-1 and Gallic Acid UEA-1 Mimetic Compounds:

Staining of normal human tissues with UEA-1 and a gallic acid UEA-1 mimetic was compared as an initial step to determine if the mimetic would also be suitable for use as a diagnostic/prognostic indicator of disease states in human tissues.

Methods:

UEA1 and the biotinylated ligand MSI 35-2 (4 copies of gallic acid; lysine scaffold) (see FIG. 5) were used in staining protocols comparable to that described above. Negative controls, performed in the absence of the primary ligand, revealed negligible background.

Results:

Table 9 summarises the normal human tissue staining profiles for UEA-1 and the UEA-1 mimetic.

TABLE 9

|  | UEA-1 | UEA-1 mimetic |
|---|---|---|
| Oesophagus | +++ | − |
| Stomach | +++ | − |
| Small intestine | +++ | ++ |
| Large intestine | +++ | +++ |
| Pancreas | +++ | − |
| Muscle | +/− | − |
| Brain | ++ | − |
| Kidney | +++ | − |

TABLE 9-continued

|  | UEA-1 | UEA-1 mimetic |
|---|---|---|
| Liver | +++ | − |
| Spleen | +++ | − |

Conclusions:

The staining profile observed using the UEA-1 mimetic on large intestine sections was comparable to that obtained using UEA-1 (as described above). This correlated well with the selection procedure for the UEA-1 mimetics, which was carried out using human Caco-2 cell membrane fractions i.e. cells which exhibit features characteristic of colonic epithelia. The UEA-1 mimetic also exhibited staining of small intestine sections as would be expected. Interestingly, no gastrointestinal or other organ tissue was stained using the UEA-1 mimetic. This was in marked contrast to UEA-1, which stained all of the tissue types, and may be a favourable factor in selection of the mimetic over UEA-1 for clinical applications.

Evaluation of Binding and Uptake of the Gallic Acid UEA-1 Mimetic into Endothelial Cells:

The gallic acid UEA-1 mimetic was compared to known cell permeable peptides in an endothelial cell permeability assay to assess it's application in a) diagnosis/prognosis of disease states (by monitoring vascularization) and b) in therapeutic delivery of pharmaceutical formulations.

Methods:
1. ECV-304 cells were seeded on round coverslips at a concentration of 2×10$^5$ cells per coverslip, on 24 well plates, and allowed to grow to confluency.
2. The serum-containing medium was replaced by serum-free medium (OptiMEM with penicillin streptomycin).
3. Aqueous stock solutions of ligands were added directly to the medium surrounding the cells to reach a final concentration of 10 μM, in 500 μl of medium.
4. One plate of samples was incubated at 37° C. in 5% CO$_2$ enriched air, and the other at 4° C. in air, both plates were incubated for 1 hr.
5. Coverslips were then given 3×5 minute washes with PBS.
6. Cells were fixed and permeabilised in 500 μl of methanol at −20° C. for 10 minutes.
7. A further 3×5 minute washes with PBS were given.
8. Non-specific binding sites were blocked by incubating the cells for 1 hr at room temperature in 500 μl of 5% milk solution in PBS (Marvel).
9. The peptides were stained with 500 μl of 15 nM Streptavidin-FITC for 1 hr at room temperature.
10. Cells were given final 3×5 minute washes with PBS.
11. The coverslips were then removed from the wells and dipped briefly in water, before being mounted on glass slides with Vectashield mounting medium for fluorescence with Dapi.

Results:

See FIG. 8 for comparison of the UEA-1 mimetic to a known cell permeable peptide and relevant controls. The UEA-1 mimetic exhibited strong staining of the nucleus with diffuse staining throughout the cytoplasm.

Conclusions:

Uptake of the UEA-1 mimetic by endothelial cells is suggestive of suitability of the mimetic for use as a marker of endothelia/blood vessels, and hence, as a diagnostic or prognostic marker in disease states.

In addition the uptake profile correlated well with that of the SynB1 peptide which is known to mediate delivery of therapeutic agents such as doxorubicin into cells. Further applications of the UEA-1 mimetic in delivery of pharmaceutical formulations through mechanisms involving direct interaction with lipid membranes (as in the case of SynB1) will be investigated.

The invention claimed is:

1. A pharmaceutical formulation comprising a pharmaceutical agent and a bioadhesive ligand, said bioadhesive ligand comprising an organocyclic moiety, said organocyclic moiety comprising a galloyl moiety wherein said organocyclic moiety is covalently linked to a scaffold moiety, said scaffold moiety comprising diaminoproprionic acid (DAP).

2. The pharmaceutical formulation of claim 1 wherein the bioadhesive ligand is covalently or noncovalently bound to a carrier entity comprising the pharmaceutical agent.

3. The pharmaceutical formulation of claim 2, wherein the carrier entity is selected from the group consisting of a nanoparticle, a microparticle, and a liposome.

4. The pharmaceutical formulation of claim 1 wherein the bioadhesive ligand comprises two or more organocyclic moieties linked by said a scaffold moiety.

5. The pharmaceutical formulation of claim 4 wherein the shortest ring-to-ring length along the scaffold and between the two organocyclic moieties is from 1 to 20 atoms.

6. The pharmaceutical formulation of claim 1 wherein the scaffold moiety comprises a peptide comprising at least 2 diaminoproprionic acid (DAP) residues.

7. The pharmaceutical formulation of claim 6 wherein said a galloyl moiety is linked to both of the at least 2 diaminoproprionic acid (DAP) residues.

8. The pharmaceutical formulation of claim 1 wherein the bioadhesive ligand comprises a compound selected from the group consisting of those compounds specified as MSI 34 #1/MSI 39 #1; MSI 34 #9; MSI 34 #13; MSI 34 #5; MSI 39#4; MSI 34 #6; MSI 34 #5; MSI 34 #17; MSI 34 #18; MSI 34 #21; and MSI 34 #22.

9. A compound selected from the group consisting of those compounds specified as MSI 34 #1/MSI 39 190 1; MSI 34 #9; MSI 34 #13; MSI 34 #5; MSI 39 #4MSI 34 #6; MSI 3 #5; MSI 34 #17; MSI 34 #18; MSI 34 #21 and MSI 34#22.

* * * * *